United States Patent
Barth et al.

(10) Patent No.: US 8,680,102 B2
(45) Date of Patent: Mar. 25, 2014

(54) PYRROLE DERIVATIVES, THEIR PREPARATION AND THEIR THERAPEUTIC APPLICATION

(75) Inventors: Francis Barth, Paris (FR); Daniel Bichon, Paris (FR); Murielle Rinaldi-Carmona, Paris (FR); Christian Congy, Paris (JP)

(73) Assignee: Sanofi, Paris (FR)

( * ) Notice: Subject to any disclaimer, the term of this patent is extended or adjusted under 35 U.S.C. 154(b) by 133 days.

(21) Appl. No.: 12/942,780

(22) Filed: Nov. 9, 2010

(65) Prior Publication Data

US 2011/0152320 A1    Jun. 23, 2011

Related U.S. Application Data

(63) Continuation of application No. PCT/FR2009/000535, filed on May 7, 2009.

(30) Foreign Application Priority Data

May 9, 2008   (FR) ..................................... 08 02552

(51) Int. Cl.
*A61K 31/496* (2006.01)
*C07D 403/02* (2006.01)

(52) U.S. Cl.
USPC ...... 514/252.13; 544/336; 544/358; 544/372; 546/184; 546/208; 548/530; 548/537; 514/247; 514/315; 514/317

(58) Field of Classification Search
USPC .................. 548/530, 537; 546/184, 192, 208; 514/315, 317, 423, 247, 252.12, 514/252.13; 544/336, 358, 372
See application file for complete search history.

(56) References Cited

U.S. PATENT DOCUMENTS

| 7,381,727 B2 * | 6/2008 | Barth et al. ............ 514/254.01 |
| 7,524,971 B2 * | 4/2009 | Barth et al. ................. 548/563 |
| 7,618,995 B2 * | 11/2009 | Barth et al. ................. 514/427 |
| 7,741,364 B2 * | 6/2010 | Faghih et al. ............... 514/428 |
| 7,879,902 B2 * | 2/2011 | Barth et al. ................. 514/423 |
| 8,044,072 B2 * | 10/2011 | Barth et al. ................. 514/326 |

FOREIGN PATENT DOCUMENTS

| WO | WO2004058249 A1 | 7/2004 |
| WO | WO2005080328 A1 | 9/2005 |

OTHER PUBLICATIONS

International Search Report relative to PCT/FR2009/00353 dated Dec. 17, 2009.

* cited by examiner

*Primary Examiner* — Golam M M Shameem
(74) *Attorney, Agent, or Firm* — Scully, Scott, Murphy & Presser, P.C.

(57) ABSTRACT

The subject of the invention is compounds of formula (I):

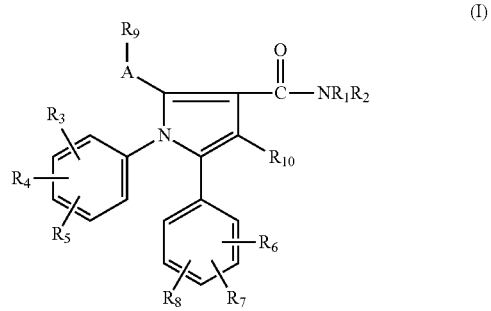

in which $R_1$-$R_{10}$ are as defined within, the method of preparation and therapeutic application as cannabinoid CB1 receptor antagonists.

7 Claims, No Drawings

PYRROLE DERIVATIVES, THEIR PREPARATION AND THEIR THERAPEUTIC APPLICATION

The present invention relates to 1,5-diphenylpyrrole-3-carboxamide derivatives, to their preparation and to their therapeutic application.

Derivatives of 1,5-diphenylpyrrole-3-carboxamide, which are active as anti-obesity agents, have been described in patent application WO 2003/027 069. Derivatives of 1,5-diphenylpyrrole-3-carboxamide, exhibiting affinity for the $CB_1$ cannabinoid receptors, have been described in patent applications WO 2004/058 249 and WO 2005/080 328. Application WO 2006/024 777 claims 4,5-diphenylpyrrole-2-carboxamides exhibiting affinity for the $CB_1$ cannabinoid receptors.

Novel 1,5-diphenylpyrrole-3-carboxamide derivatives carrying a particular substituent at the 2-position of the pyrrole have now been found which possess antagonist properties for the $CB_1$ cannabinoid receptors. In particular, these novel derivatives have antagonist properties for the peripheral $CB_1$ receptors and exhibit low penetration at the level of the brain.

The subject of the present invention is compounds corresponding to the formula:

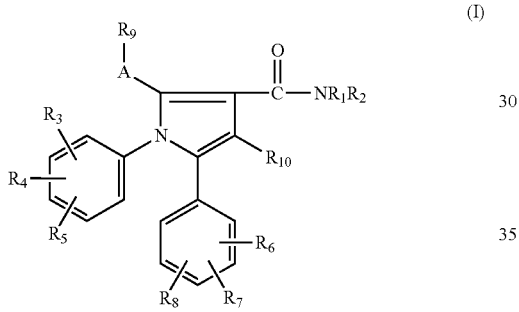

(I)

in which:

A represents a $(C_1-C_6)$alkylene group which is unsubstituted or substituted one or more times with a $(C_1-C_3)$ alkyl group or a fluorine atom;

$R_1$ represents a hydrogen atom or a $(C_1-C_4)$alkyl group which is unsubstituted or substituted with one or more fluorine atoms;

$R_2$ represents:
  either a homopiperidin-1-yl, piperidin-1-yl, pyrrolidin-1-yl or azetidin-1-yl radical, the said radicals being unsubstituted or substituted once or twice with a substituent each independently chosen from a fluorine atom, a group $(C_1-C_4)$alkoxyl, $(C_1-C_4)$alkyl, trifluoromethyl, —$OCF_3$, —$CH_2OH$, —$CONH_2$ and/or a phenyl group, the said phenyl group being unsubstituted or substituted once or twice with a substituent each independently chosen from a halogen atom, a —$CF_3$ group, a methoxyl group and/or a trifluoromethoxyl group;
  or an amino$(C_1-C_6)$alkyl group which is unsubstituted or substituted with one or several substituents each independently chosen from a fluorine atom, a hydroxyl group, a —$CONH_2$ group and/or a phenyl group, the said phenyl group being unsubstituted or substituted once or twice with a substituent each independently chosen from a halogen atom, a —$CF_3$ group, a methoxyl group and/or a trifluoromethoxyl group;

or $R_1$ and $R_2$ together with the nitrogen atom to which they are attached constitute:
  either a piperazin-1-yl or 1,4-diazepan-1-yl radical, the said radicals being unsubstituted or substituted with a phenyl, benzodioxolyl, benzodioxolylmethyl, tetrahydrofuranylcarbonyl, —$COR_{11}$, and/or —$CH_2COR_{11}$ group; the phenyl group being itself unsubstituted or substituted once or several times with a substituent each independently chosen from a halogen atom, a $(C_1-C_4)$alkyl, trifluoromethyl, hydroxyl, $(C_1-C_4)$alkoxyl and/or cyano group;
  or a homopiperidin-1-yl, piperidin-1-yl, pyrrolidin-1-yl or azetidin-1-yl radical, the said radicals being unsubstituted or substituted once or twice with a substituent each independently chosen from:
    a fluorine atom, a cyano, —$COR_{11}$, —$CONR_{12}R_{13}$, —$NR_{12}R_{13}$, —$NHCOR_{14}$, —$CH_2COR_{11}$, —$SO_2R_{14}$ group; and/or —$SO_2 NR_{12}R_{13}$;
    and/or a $(C_1-C_4)$alkyl group which is unsubstituted or substituted with one or more substituents each independently chosen from a halogen atom and/or a hydroxyl,
    and/or a phenyl or pyridinyl group; the said groups being unsubstituted or substituted once or several times with a substituent each independently chosen from a halogen atom, a $(C_1-C_4)$alkyl, trifluoromethyl, hydroxyl, $(C_1-C_4)$alkoxyl and/or cyano group;
    and/or a benzyl group which is unsubstituted or substituted once or several times with a substituent each independently chosen from a halogen atom, a $(C_1-C_4)$ alkyl, trifluoromethyl, hydroxyl, $(C_1-C_4)$alkoxyl and/or cyano group;
    and/or a piperidin-1-yl, pyrrolidin-1-yl or azetidin-1-yl group, the said groups being unsubstituted or substituted once or several times with a substituent each independently chosen from a fluorine atom, a $(C_1-C_4)$ alkyl, $(C_1-C_4)$alkoxyl, hydroxyl, trifluoromethyl and/or —$OCF_3$ group;
    and/or an aminophenyl or aminobenzyl group, the said groups being unsubstituted or substituted once or several times with a substituent each independently chosen from a halogen atom, a methyl, trifluoromethyl, hydroxyl, $(C_1-C_4)$alkoxyl and/or cyano group;
    and/or an amino$(C_3-C_7)$cycloalkyl group which is unsubstituted or substituted once or several times with a substituent each independently chosen from a halogen atom, a hydroxyl, $(C_1-C_4)$alkyl, $(C_1-C_4)$ alkoxyl and/or cyano group, the said $(C_1-C_4)$alkyl group being unsubstituted or substituted once or several times with a fluorine atom;

$R_3$, $R_4$, $R_5$, $R_6$, $R_7$, $R_8$ each independently represent a hydrogen atom, a halogen atom, a —CN, —$S(O)_nR_{14}$ or —$OS(O)_nR_{14}$ group, or a $(C_1-C_6)$alkyl group which is unsubstituted or substituted once or several times with a substituent each independently chosen from a fluorine atom, an —OH, —$OR_{14}$, —$S(O)_nR_{14}$, —$OSO_2R_{14}$ and/or —$NHSO_2R_{14}$ group, or a $(C_1-C_6)$alkoxyl group, which is unsubstituted or substituted with one or more substituents each independently chosen from a fluorine atom, an —OH, —$OR_{14}$, —$S(O)_nR_{14}$, —$OSO_2R_{14}$ and/or —$NHSO_2R_{14}$ group;

$R_9$ represents an —$OR_{12}$, —CN, —$CO_2H$, $NR_{12}R_{13}$, —$CONR_{12}R_{13}$, —$NR_1COR_{12}$, —$CONHNH_2$, —$CONHOH$, —$CONHSO_2R_{14}$, —$S(O)_nR_{14}$, —$SO_2NR_{12}R_{13}$, —$NR_{18}SO_2R_{14}$ or —$NR_{15}SO_2NR_{12}R_{13}$ group, or an aromatic heterocycle chosen from:

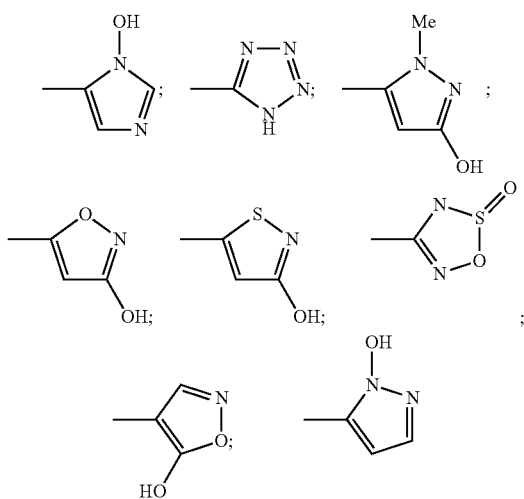

$R_{10}$ represents a hydrogen or a $(C_1-C_4)$alkyl group;
$R_{11}$ represents:
   a $(C_1-C_4)$alkyl, phenyl, benzyl, $(C_1-C_4)$alkoxyl, or $(C_1-C_3)$alkylene-O—$(C_1-C_3)$alkyl group, the said groups being unsubstituted or substituted with one or more substituents each independently chosen from a $(C_1-C_4)$alkoxyl group, a hydroxyl group and/or a fluorine atom;
   a trifluoromethyl;
   and/or an $NR_{16}R_{17}$ group;
$R_{12}$ and $R_{13}$ each independently represent a hydrogen atom or a $(C_1-C_6)$alkyl group optionally substituted with one or more substituents each independently chosen from a halogen atom, a $(C_3-C_7)$cycloalkyl, cyano, —OH and/or —$OR_{14}$ group;
or $R_{12}$ and $R_{13}$ together with the nitrogen atom to which they are attached constitute a 4- to 7-membered heterocyclic radical which may contain a second heteroatom chosen from a nitrogen, oxygen or sulphur atom;
n represents 0, 1 or 2;
$R_{14}$ represents a $(C_1-C_4)$alkyl group which is unsubstituted or substituted with one or more fluorine atoms;
$R_{15}$ represents a hydrogen atom or a $(C_1-C_4)$alkyl group;
$R_{16}$ and $R_{17}$ each independently represent:
   a hydrogen atom;
   and/or a benzyl group which is unsubstituted or substituted once or several times with a substituent each independently chosen from a halogen atom, a methyl, trifluoromethyl, hydroxyl, $(C_1-C_4)$alkoxyl and/or cyano group;
   and/or a $(C_1-C_6)$alkyl group which is optionally substituted with one or more substituents each independently chosen from a halogen atom, a $(C_3-C_7)$cycloalkyl, cyano —OH, and/or —$OR_{14}$ group;
$R_{18}$ represents a hydrogen atom or a $(C_1-C_4)$alkyl group which is unsubstituted or substituted with one or more fluorine atoms;
in the form of bases (=correspond to the free forms of the compounds) and the salts thereof which are pharmaceutically acceptable or acceptable for the purification and/or isolation of the said compounds of formula (I).

The compounds of formula (I) may contain one or more asymmetric carbon atoms. They can therefore exist in the form of enantiomers or diastereoisomers. These enantiomers, diastereoisomers and mixtures thereof, including the racemic mixtures, form part of the invention.

The compounds of formula (I) may exist in the form of bases (that is to say as they are in their free forms), of addition salts with acids or of addition salts with bases. These salts are advantageously prepared with pharmaceutically acceptable salts but the salts of other acids which are useful, for example, for the purification or isolation of the compounds of formula (I) also form part of the invention.

The expression $(C_1-C_3)$alkyl, $(C_1-C_4)$alkyl or $(C_1-C_6)$alkyl group is understood to mean respectively a linear or branched alkyl radical of one to three carbon atoms, of one to four carbon atoms or of one to six carbon atoms, such as the methyl, ethyl, propyl, isopropyl, butyl, isobutyl, sec-butyl, tert-butyl, pentyl, isopentyl, n-hexyl or isohexyl radical. The methyl group is preferred for a $(C_1-C_3)$alkyl, for a $(C_1-C_4)$alkyl and for a $(C_1-C_6)$alkyl.

The expression $(C_1-C_3)$alkylene or $(C_1-C_6)$alkylene group is understood to mean respectively a linear bivalent carbon radical of one to three carbon atoms or of one to six carbon atoms such as —$(CH_2)$—, —$(CH_2)_2$—, —$(CH_2)_3$—, —$(CH_2)_4$—, —$(CH_2)_5$— and —$(CH_2)_6$.

The expression $(C_1-C_4)$alkoxyl is understood to mean an oxygen atom attached to a linear or branched carbon radical of one to four carbon atoms such as methoxyl, ethoxy, propoxy, isopropoxy, butoxy, sec-butoxy or tert-butoxy radical. The methoxyl group is preferred.

The expression halogen atom is understood to mean a fluorine, chlorine, bromine or iodine atom, the fluorine, chlorine or bromine atoms being preferred.

The expression $(C_3-C_7)$cycloalkyl group is understood to mean a cyclopropyl, cyclobutyl, cyclopentyl, cyclohexyl or cycloheptyl radical.

The expression amino-cycloalkyl group is understood to mean, for the cycloalkyl part, a cyclopropyl, cyclobutyl, cyclopentyl, cyclohexyl or cycloheptyl carbon radical.

The expression 4- to 7-membered saturated or unsaturated heterocyclic radical, containing or not containing a second heteroatom such as O, N or S, is understood to mean in particular radicals such as homopiperidin-1-yl, morpholin-4-yl, piperidin-1-yl, piperazin-1-yl, pyrrolidin-1-yl, azetidin-1-yl, the piperidin-1-yl and pyrrolidin-1-yl radicals being preferred.

According to a first variant of the invention, the compounds of formula (IA) are differentiated in which:
$R_1$ represents a hydrogen atom or a $(C_1-C_4)$alkyl group which is unsubstituted or substituted with one or more fluorine atoms;
$R_2$ represents:
   either a homopiperidin-1-yl, piperidin-1-yl, pyrrolidin-1-yl or azetidin-1-yl radical, the said radicals being substituted once or twice with a substituent each independently chosen from a fluorine atom, a group $(C_1-C_4)$alkoxyl, $(C_1-C_4)$alkyl, trifluoromethyl, —$OCF_3$, —$CH_2OH$, —$CONH_2$ and/or a phenyl group, the said phenyl group being unsubstituted or substituted once or twice with a substituent each independently chosen from a halogen atom, a —$CF_3$ group, a methoxyl group and/or a trifluoromethoxyl group;
   or an amino$(C_1-C_6)$alkyl group which is substituted with one or several substituents each independently chosen from a fluorine atom, a hydroxyl group, a —$CONH_2$ group and/or a phenyl group, the said phenyl group being unsubstituted or substituted once or twice with a substituent each independently chosen from a halogen atom, a —$CF_3$ group, a methoxyl group and/or a trifluoromethoxyl group;

the other substituents being as defined for the compounds of formula (I).

According to this first variant (IA), preference is given to the compounds in which the radical $R_2$ represents a homopiperidin-1-yl, piperidin-1-yl, pyrrolidin-1-yl or azetidin-1-yl radical, the said radicals being substituted once or twice with a substituent each independently chosen from a fluorine atom, a ($C_1$-$C_4$)alkoxyl, trifluoromethyl, —$OCF_3$, —$CH_2OH$ or —$CONH_2$ group and/or a phenyl group, the said phenyl group being unsubstituted or substituted once or twice with a substituent each independently chosen from a halogen atom, a —$CF_3$ group, a methoxyl group and/or a trifluoromethoxyl group.

According to this first variant (IA), preference is given to the compounds in which $R_1$ represents a hydrogen atom.

According to a second variant of the invention, the compounds of formula (IB) are differentiated in which $R_1$ and $R_2$ together with the nitrogen atom to which they are attached constitute:

either a piperazin-1-yl or 1,4-diazepan-1-yl radical, the said radicals being substituted with a phenyl, benzodioxolyl, benzodioxolylmethyl, tetrahydrofuranylcarbonyl, —$COR_{11}$, and/or —$CH_2COR_{11}$ group; the phenyl group being itself substituted once or several times with a substituent each independently chosen from a halogen atom, a methyl, trifluoromethyl, hydroxyl, ($C_1$-$C_4$) alkoxyl and/or cyano group;

or a homopiperidin-1-yl, piperidin-1-yl, pyrrolidin-1-yl or azetidin-1-yl radical, the said radicals being substituted once or twice with a substituent each independently chosen from:

a fluorine atom, a cyano, —$COR_{11}$, —$CONR_{12}R_{13}$, —$NR_{12}R_{13}$, —$NHCOR_{14}$, —$CH_2COR_{11}$, —$SO_2R_{14}$ group; and/or —$SO_2NR_{12}R_{13}$;

and/or a ($C_1$-$C_4$)alkyl group which is unsubstituted or substituted with one or more substituents each independently chosen from a halogen atom and/or a hydroxyl, and/or a phenyl or pyridinyl group; the said groups being unsubstituted or substituted once or several times with a substituent each independently chosen from a halogen atom, a methyl, trifluoromethyl, hydroxyl, ($C_1$-$C_4$)alkoxyl and/or cyano group;

and/or a benzyl group which is substituted once or several times with a substituent each independently chosen from a halogen atom, a methyl, trifluoromethyl, hydroxyl, ($C_1$-$C_4$)alkoxyl and/or cyano group;

and/or a piperidin-1-yl, pyrrolidin-1-yl or azetidin-1-yl group, the said groups being unsubstituted or substituted once or several times with a substituent each independently chosen from a fluorine atom, a ($C_1$-$C_4$)alkyl, ($C_1$-$C_4$)alkoxyl, hydroxyl, trifluoromethyl and/or —$OCF_3$ group;

and/or an aminophenyl or aminobenzyl group, the said groups being unsubstituted or substituted once or several times with a substituent each independently chosen from a halogen atom, a methyl, trifluoromethyl, hydroxyl, ($C_1$-$C_4$)alkoxyl and/or cyano group;

and/or an amino($C_3$-$C_7$)cycloalkyl group which is unsubstituted or substituted once or several times with a substituent each independently chosen from a halogen atom, a hydroxyl, ($C_1$-$C_4$)alkyl, ($C_1$-$C_4$)alkoxyl and/or cyano group, the said ($C_1$-$C_4$)alkyl group being unsubstituted or substituted once or several times with a fluorine atom;

the other substituents being as defined for the compounds of formula (I).

According to this second variant, preference is given to the compounds in which:

$R_1$ and $R_2$ together with the nitrogen atom to which they are attached constitute a homopiperidin-1-yl, piperidin-1-yl, pyrrolidin-1-yl or azetidin-1-yl radical, the said radical being substituted once or twice with a substituent each independently chosen from:

a fluorine atom, a cyano, —$COR_{11}$, —$CONR_{12}R_{13}$, —$NR_{12}R_{13}$, —$NHCOR_{14}$, —$CH_2COR_{11}$, —$SO_2R_{14}$ group; and/or —$SO_2NR_{12}R_{13}$;

and/or a ($C_1$-$C_4$)alkyl group which is unsubstituted or substituted with one or more substituents each independently chosen from a halogen atom and/or a hydroxyl, and/or a phenyl or pyridinyl group; the said groups being unsubstituted or substituted once or several times with a substituent each independently chosen from a halogen atom, a ($C_1$-$C_4$)alkyl, trifluoromethyl, hydroxyl, ($C_1$-$C_4$)alkoxyl and/or cyano group;

and/or a benzyl group which is substituted once or several times with a substituent each independently chosen from a halogen atom, a ($C_1$-$C_4$)alkyl, trifluoromethyl, hydroxyl, ($C_1$-$C_4$)alkoxyl and cyano group;

and/or a piperidin-1-yl, pyrrolidin-1-yl or azetidin-1-yl group, the said groups being unsubstituted or substituted once or several times with a substituent each independently chosen from a fluorine atom, a ($C_1$-$C_4$) alkyl, ($C_1$-$C_4$)alkoxyl, hydroxyl, trifluoromethyl and/or —$OCF_3$ group;

and/or an aminophenyl or aminobenzyl group, the said groups being unsubstituted or substituted once or several times with a substituent each independently chosen from a halogen atom, a ($C_1$-$C_4$)alkyl, trifluoromethyl, hydroxyl, ($C_1$-$C_4$)alkoxyl and/or cyano group;

and/or an amino($C_3$-$C_7$)cycloalkyl group which is unsubstituted or substituted once or several times with a substituent each independently chosen from a halogen atom, a hydroxyl, ($C_1$-$C_4$)alkyl, ($C_1$-$C_4$) alkoxyl and/or cyano group, the said ($C_1$-$C_4$)alkyl group being unsubstituted or substituted once or several times with a fluorine atom;

the other substituents being as defined for the compounds of formula (I).

According to this second variant (IB), preference is given in particular to the compounds in which $R_1$ and $R_2$ together with the nitrogen atom to which they are attached constitute a piperidin-1-yl radical which is substituted once or twice with a substituent. The substituent(s) are each independently chosen from those indicated above for this second variant (IB).

For the 2 variants according to the invention, preference is given to the compounds in which:

A represents an unsubstituted ($C_1$-$C_5$)alkylene group;

$R_9$ represents an —$OR_{12}$, —$NR_{12}R_{13}$, —$CONR_{12}R_{13}$, —$NR_{15}COR_{12}$, —$CONHNH_2$, —$CONHOH$, —$S(O)_n R_{14}$, —$SO_2NR_{12}R_{13}$, —$NR_{18}SO_2R_{14}$, or —$NR_{15}SO_2NR_{12}R_{13}$ group;

the other substituents being as defined above for the compounds of formula (I).

In particular, for $R_9$, preference is given to an —$OR_{12}$, —$NR_{12}R_{13}$, —$CONR_{12}R_{13}$, —$NR_{15}COR_{12}$ or —$NR_{18}SO_2R_{14}$ group. As regards the –$OR_{12}$ and —$NR_{12}R_{13}$ groups, preference is given more particularly to $R_{12}$ and $R_{13}$ which are different from hydrogen.

According to the present invention, preference is given to the compounds in which $R_{10}$ represents a hydrogen.

Among the compounds according to the invention, mention may be made in particular of the compounds below, as they are and the salts thereof:

| Chemical structure | IUPAC name (ACDName) |
|---|---|
| 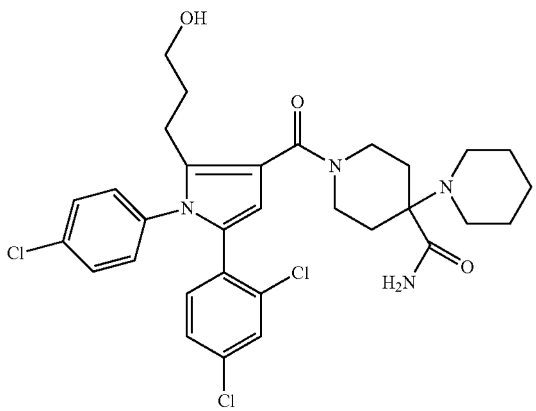 [SMILES: NC(=O)C1(N2CCCCC2)CCN(C(=O)c2cc(-c3ccc(Cl)cc3Cl)n(-c3ccc(Cl)cc3)c2CCCO)CC1] | 1'-{(1-(4-chlorophenyl)-5-(2,4-dichlorophenyl)-2-(3-hydroxypropyl)-1H-pyrrol-3-yl]carbonyl}-1,4'-bipiperidine-4'-carboxamide |
| 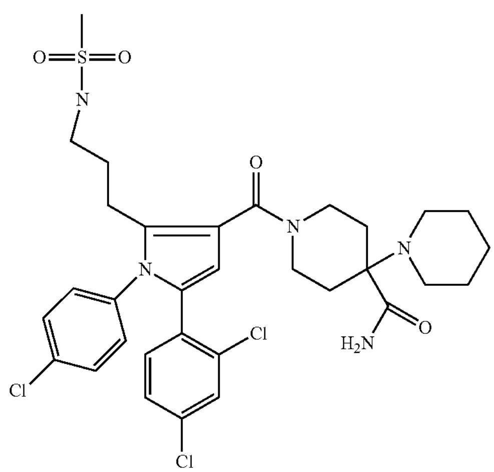 [SMILES: CS(=O)(=O)NCCCc1c(C(=O)N2CCC(C(N)=O)(N3CCCCC3)CC2)cc(-c2ccc(Cl)cc2Cl)n1-c1ccc(Cl)cc1] | 1-{[1-(4-chlorophenyl)-5-(2,4-dichlorophenyl)-2-{3-[(methylsulfphonyl)amino]propyl}-1H-pyrrol-3-yl]carbonyl}-1,4'-bipiperidine-4'-carboxamide |
| 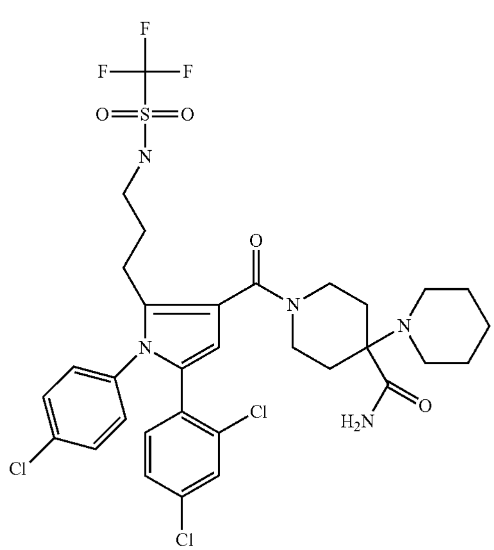 [SMILES: NC(=O)C1(N2CCCCC2)CCN(C(=O)c2cc(-c3ccc(Cl)cc3Cl)n(-c3ccc(Cl)cc3)c2CCCNS(=O)(=O)C(F)(F)F)CC1] | 1'-{[1-(4-chlorophenyl)-5-(2,4-dichlorophenyl)-2-(3-{[(trifluoromethyl)sulfonyl]amino}-propyl)-1H-pyrrol-3-yl]carbonyl}-1,4'-bipiperidine-4'-carboxamide |

| Chemical structure | IUPAC name (ACDName) |
|---|---|
| 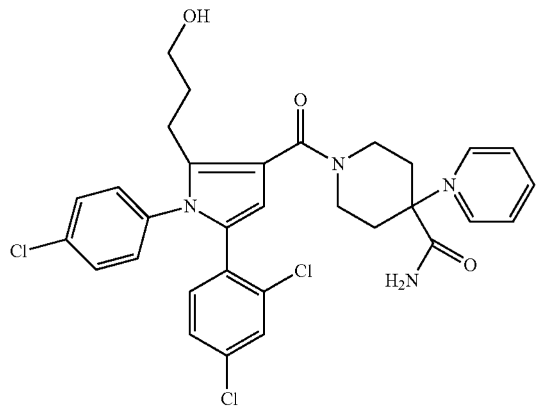 | 1-{[1-(4-chlorophenyl)-5-(2,4-dichlorophenyl)-2-(3-hydroxypropyl)-1H-pyrrol-3-yl]carbonyl}-4-phenylpiperidine-4-carboxamide |
| 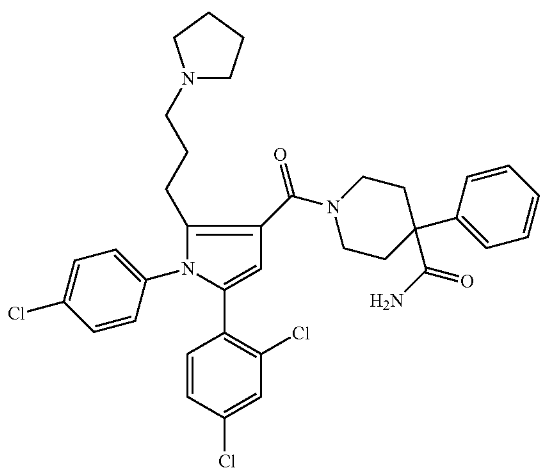 [SMILES: NC(=O)C1(c2ccccc2)CCN(C(=O)c2cc(-c3ccc(Cl)cc3Cl)n(-c3ccc(Cl)cc3)c2CCCN2CCCC2)CC1] | 1-{[1-(4-chlorophenyl)-5-(2,4-dichlorophenyl)-2-(3-pyrrolidin-1-ylpropyl)-1H-pyrrol-3-yl]carbonyl}-4-phenylpiperidine-4-carboxamide |
| 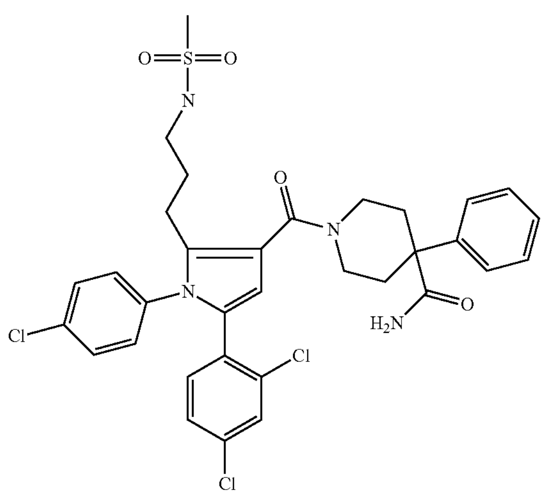 [SMILES: CS(=O)(=O)NCCCc1c(C(=O)N2CCC(C(N)=O)(c3ccccc3)CC2)cc(-c2ccc(Cl)cc2Cl)n1-c1ccc(Cl)cc1] | 1-{[1-(4-chlorophenyl)-5-(2,4-dichlorophenyl)-2-{3-[(methylsulphonyl)amino]propyl}-1H-pyrrol-3-yl]carbonyl}-4-phenylpiperidine-4-carboxamide |

| Chemical structure | IUPAC name (ACDName) |
|---|---|
| 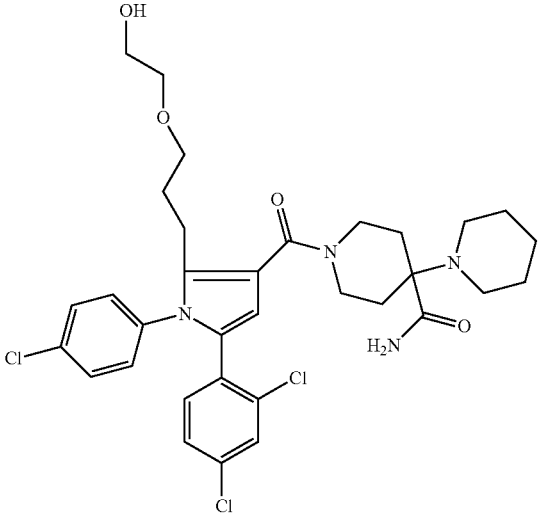 [SMILES: NC(=O)C1(N2CCCCC2)CCN(C(=O)c2cc(-c3ccc(Cl)cc3Cl)n(-c3ccc(Cl)cc3)c2CCCOCCO)CC1] | 1'-({1-(4-chlorophenyl)-5-(2,4-dichlorophenyl)-2-[3-(2-hydroxyethoxy)propyl]-1H-pyrrol-3-yl}carbonyl)-1,4'-bipiperidine-4'-carboxamide |
| 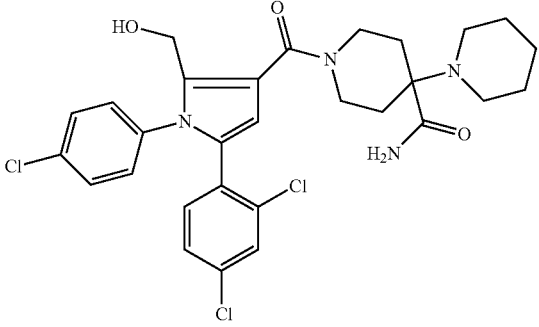 [SMILES: NC(=O)C1(N2CCCCC2)CCN(C(=O)c2cc(-c3ccc(Cl)cc3Cl)n(-c3ccc(Cl)cc3)c2CO)CC1] | 1'-{[1-(4-chlorophenyl)-5-(2,4-dichlorophenyl)-2-(hydroxymethyl)-1H-pyrrol-3-yl]carbonyl}-1,4'-bipiperidine-4'-carboxamide |
| 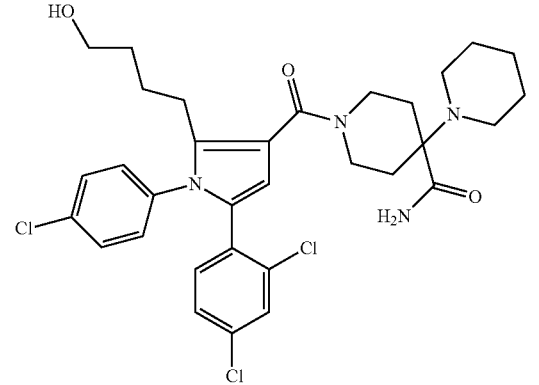 [SMILES: NC(=O)C1(N2CCCCC2)CCN(C(=O)c2cc(-c3ccc(Cl)cc3Cl)n(-c3ccc(Cl)cc3)c2CCCCO)CC1] | 1'-{[1-(4-chlorophenyl)-5-(2,4-dichlorophenyl)-2-(4-hydroxybutyl)-1H-pyrrol-3-yl]carbonyl}-1,4'-bipiperidine-4'-carboxamide |

-continued

| Chemical structure | IUPAC name (ACDName) |
|---|---|
| 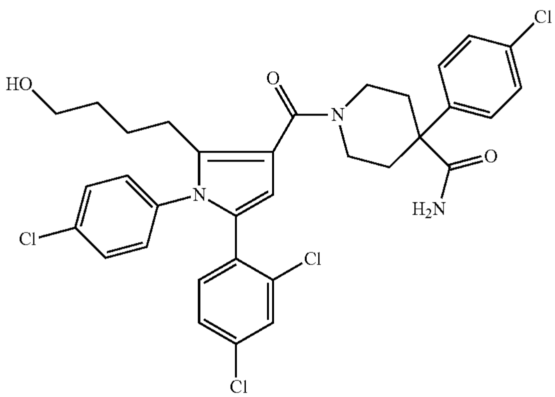 [SMILES: NC(=O)C1(c2ccc(Cl)cc2)CCN(C(=O)c2cc(-c3ccc(Cl)cc3Cl)n(-c3ccc(Cl)cc3)c2CCCCO)CC1] | 4-(4-chlorophenyl)-1-{[1-(4-chlorophenyl)-5-(2,4-dichlorophenyl)-2-(4-hydroxybutyl)-1H-pyrrol-3-yl]carbonyl}piperidine-4-carboxamide |
| 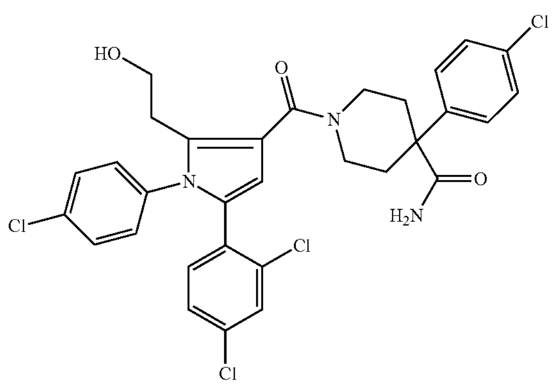 [SMILES: NC(=O)C1(c2ccc(Cl)cc2)CCN(C(=O)c2cc(-c3ccc(Cl)cc3Cl)n(-c3ccc(Cl)cc3)c2CCO)CC1] | 4-(4-chlorophenyl)-1-{[1-(4-chlorophenyl)-5-(2,4-dichlorophenyl)-2-(2-hydroxyethyl)-1H-pyrrol-3-yl]carbonyl}piperidine-4-carboxamide |
| 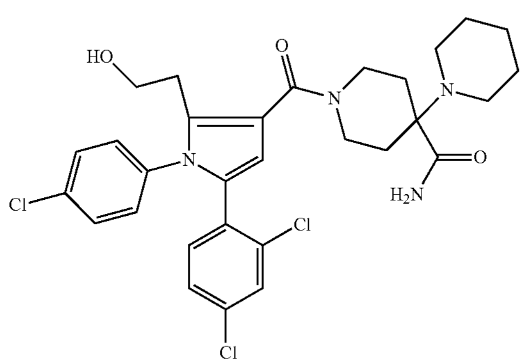 [SMILES: NC(=O)C1(N2CCCCC2)CCN(C(=O)c2cc(-c3ccc(Cl)cc3Cl)n(-c3ccc(Cl)cc3)c2CCO)CC1] | 1'-{[1-(4-chlorophenyl)-5-(2,4-dichlorophenyl)-2-(2-hydroxyethyl)-1H-pyrrol-3-yl]carbonyl}-1,4'-bipiperidine-4'-carboxamide |
| 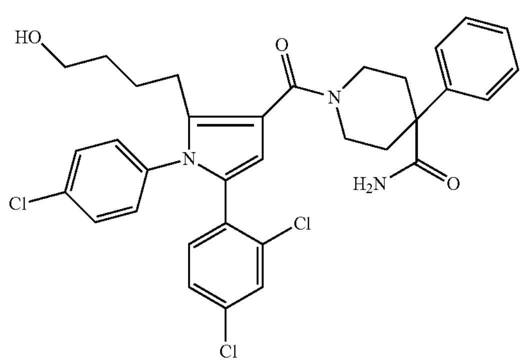 [SMILES: NC(=O)C1(c2ccccc2)CCN(C(=O)c2cc(-c3ccc(Cl)cc3Cl)n(-c3ccc(Cl)cc3)c2CCCCO)CC1] | 1-{[1-(4-chlorophenyl)-5-(2,4-dichlorophenyl)-2-(4-hydroxybutyl)-1H-pyrrol-3-yl]carbonyl}-4-phenylpiperidine-4-carboxamide |

| Chemical structure | IUPAC name (ACDName) |
|---|---|
| 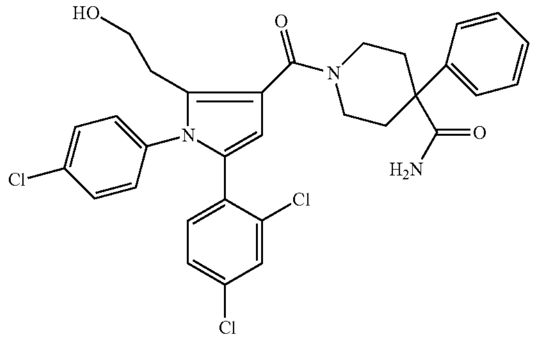 [SMILES: NC(=O)C1(c2ccccc2)CCN(C(=O)c2cc(-c3ccc(Cl)cc3Cl)n(-c3ccc(Cl)cc3)c2CCO)CC1] | 1-{[1-(4-chlorophenyl)-5-(2,4-dichlorophenyl)-2-(2-hydroxyethyl)-1H-pyrrol-3-yl]carbonyl}-4-phenylpiperidine-4-carboxamide |
| 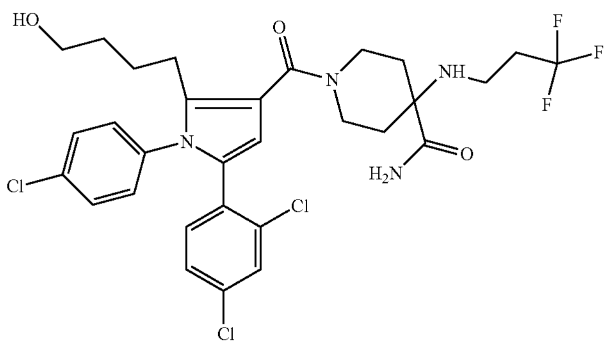 [SMILES: NC(=O)C1(NCCC(F)(F)F)CCN(C(=O)c2cc(-c3ccc(Cl)cc3Cl)n(-c3ccc(Cl)cc3)c2CCCCO)CC1] | 4-amino-1-{[1-(4-chlorophenyl)-5-(2,4-dichlorophenyl)-2-(4-hydroxybutyl)-1H-pyrrol-3-yl]carbonyl}piperidine-4-carboxamide-1,1,1-trifluorobutane (1:1) |
| 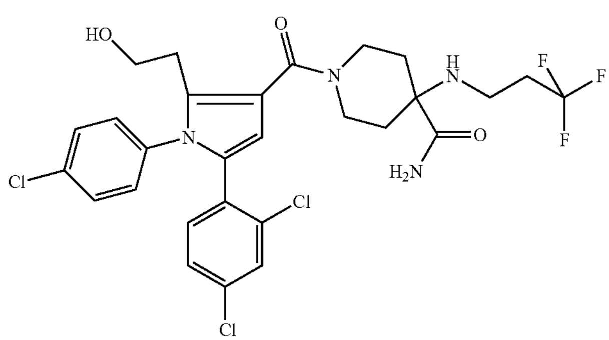 [SMILES: NC(=O)C1(NCCC(F)(F)F)CCN(C(=O)c2cc(-c3ccc(Cl)cc3Cl)n(-c3ccc(Cl)cc3)c2CCO)CC1] | 1{[1-(4-chlorophenyl)-5-(2,4-dichlorophenyl)-2-(2-hydroxyethyl)-1H-pyrrol-3-yl]carbonyl}-4-[(3,3,3-trifluoropropyl)amino]piperidine-4-carboxamide |
| 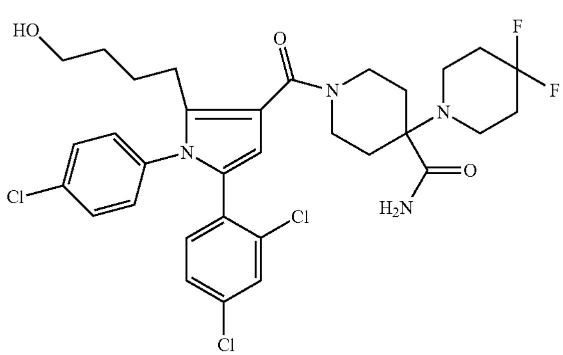 [SMILES: NC(=O)C1(N2CCC(F)(F)CC2)CCN(C(=O)c2cc(-c3ccc(Cl)cc3Cl)n(-c3ccc(Cl)cc3)c2CCCCO)CC1] | 1'-{[1-(4-chlorophenyl)-5-(2,4-dichlorophenyl)-2-(4-hydroxybutyl)-1H-pyrrol-3-yl]carbonyl}-4,4-difluoro-1,4'-bipiperidine-4'-carboxamide |

| Chemical structure | IUPAC name (ACDName) |
|---|---|
| 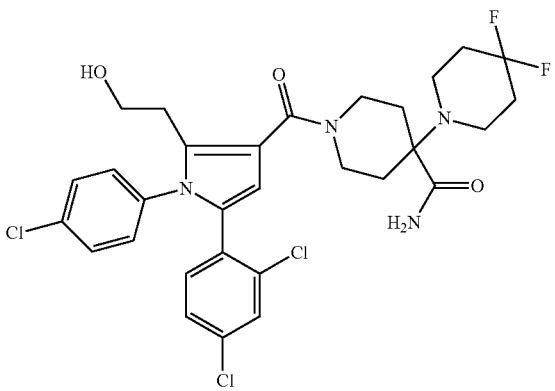 [SMILES: NC(=O)C1(N2CCC(F)(F)CC2)CCN(C(=O)c2cc(-c3ccc(Cl)cc3Cl)n(-c3ccc(Cl)cc3)c2CCO)CC1] | 1'-{[1-(4-chlorophenyl)-5-(2,4-dichlorophenyl)-2-(2-hydroxyethyl)-1H-pyrrol-3-yl]carbonyl}-4,4-difluoro-1,4'-bipiperidine-4'-carboxamide |
| 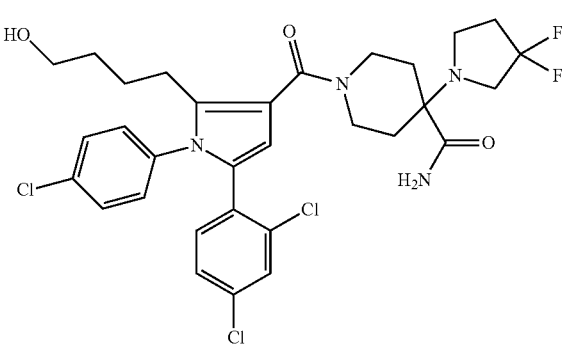 [SMILES: NC(=O)C1(N2CCC(F)(F)C2)CCN(C(=O)c2cc(-c3ccc(Cl)cc3Cl)n(-c3ccc(Cl)cc3)c2CCCCO)CC1] | 1-{[1-(4-chlorophenyl)-5-(2,4-dichlorophenyl)-2-(4-hydroxybutyl)-1H-pyrrol-3-yl]carbonyl}-4-(3,3-difluoropyrrolidin-1-yl)piperidine-4-carboxamide |
| 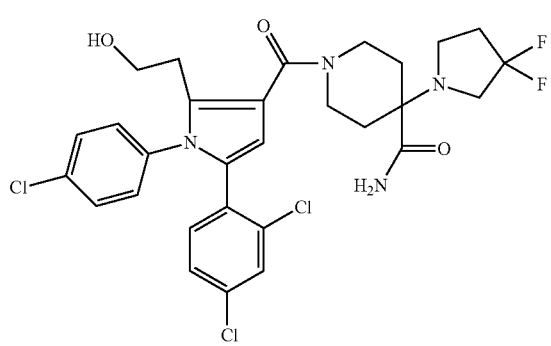 [SMILES: NC(=O)C1(N2CCC(F)(F)C2)CCN(C(=O)c2cc(-c3ccc(Cl)cc3Cl)n(-c3ccc(Cl)cc3)c2CCO)CC1] | 1-{[1-(4-chlorophenyl)-5-(2,4-dichlorophenyl)-2-(2-hydroxyethyl)-1H-pyrrol-3-yl]carbonyl}-4-(3,3-difluoropyrrolidin-1-yl)piperidine-4-carboxamide |
| 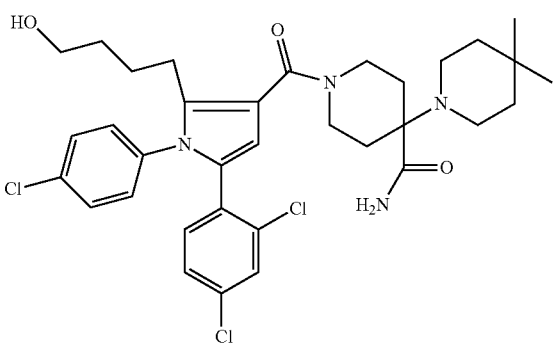 [SMILES: CC1(C)CCN(C2(C(N)=O)CCN(C(=O)c3cc(-c4ccc(Cl)cc4Cl)n(-c4ccc(Cl)cc4)c3CCCCO)CC2)CC1] | 1'-{[1-(4-chlorophenyl)-5-(2,4-dichlorophenyl)-2-(4-hydroxybutyl)-1H-pyrrol-3-yl]carbonyl}-4,4-dimethyl-1,4'-bipiperidine-4'-carboxamide |

| Chemical structure | IUPAC name (ACDName) |
|---|---|
| 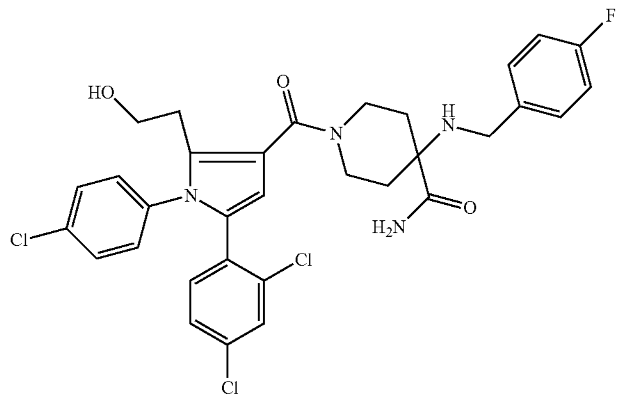 [SMILES: NC(=O)C1(NCc2ccc(F)cc2)CCN(C(=O)c2cc(-c3ccc(Cl)cc3Cl)n(-c3ccc(Cl)cc3)c2CCO)CC1] | 1-{[1-(4-chlorophenyl)-5-(2,4-dichlorophenyl)-2-(2-hydroxyethyl)-1H-pyrrol-3-yl]carbonyl}-4-[(4-fluorobenzyl)amino]piperidine-4-carboxamide |
| 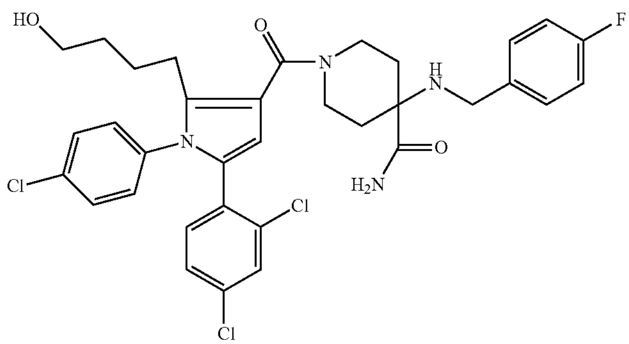 [SMILES: NC(=O)C1(NCc2ccc(F)cc2)CCN(C(=O)c2cc(-c3ccc(Cl)cc3Cl)n(-c3ccc(Cl)cc3)c2CCCCO)CC1] | 1-{[1-(4-chlorophenyl)-5-(2,4-dichlorophenyl)-2-(4-hydroxybutyl)-1H-pyrrol-3-yl]carbonyl}-4-[(4-fluorobenzyl)amino]piperidine-4-carboxamide |
| 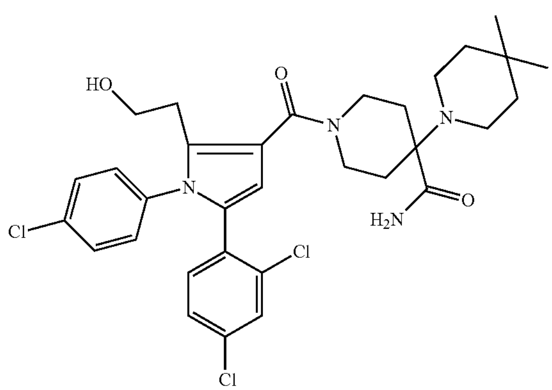 [SMILES: CC1(C)CCN(C2(C(N)=O)CCN(C(=O)c3cc(-c4ccc(Cl)cc4Cl)n(-c4ccc(Cl)cc4)c3CCO)CC2)CC1] | 1'-{[1-(4-chlorophenyl)-5-(2,4-dichlorophenyl)-2-(2-hydroxyethyl)-1H-pyrrol-3-yl]carbonyl}-4,4-dimethyl-1,4'-bipiperidine-4'-carboxamide |
| 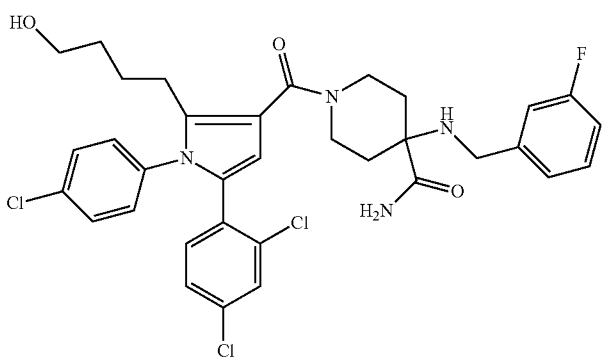 [SMILES: NC(=O)C1(NCc2cccc(F)c2)CCN(C(=O)c2cc(-c3ccc(Cl)cc3Cl)n(-c3ccc(Cl)cc3)c2CCCCO)CC1] | 1-{[1-(4-chlorophenyl)-5-(2,4-dichlorophenyl)-2-(4-hydroxybutyl)-1H-pyrrol-3-yl]carbonyl}-4-[(3-fluorobenzyl)amino]piperidine-4-carboxamide |

| Chemical structure | IUPAC name (ACDName) |
|---|---|
| 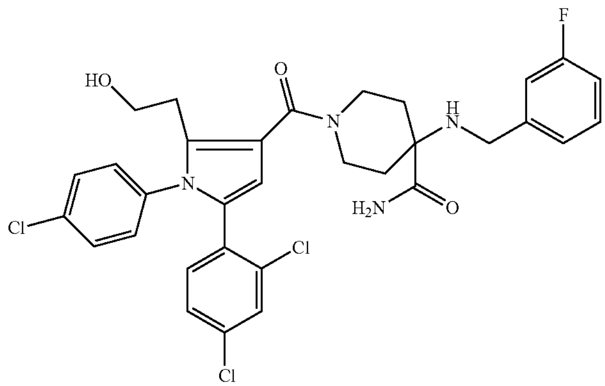 [SMILES: NC(=O)C1(NCc2cccc(F)c2)CCN(C(=O)c2cc(-c3ccc(Cl)cc3Cl)n(-c3ccc(Cl)cc3)c2CCO)CC1] | 1-{[1-(4-chlorophenyl)-5-(2,4-dichlorophenyl)-2-(2-hydroxyethyl)-1H-pyrrol-3-yl]carbonyl}-4-[(3-fluorobenzyl)amino]piperidine-4-carboxamide |
| 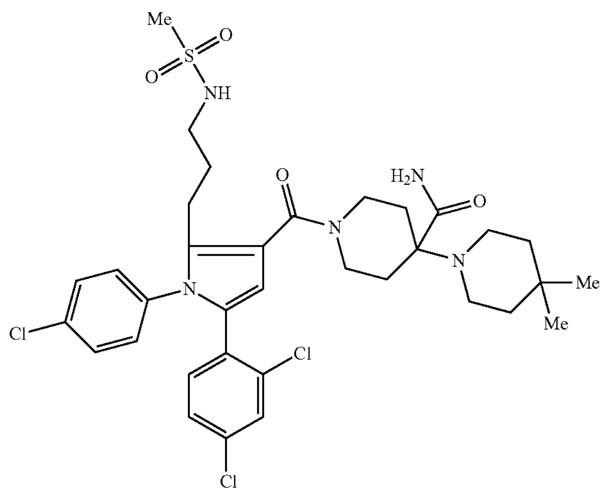 [SMILES: CC1(C)CCN(C2(C(N)=O)CCN(C(=O)c3cc(-c4ccc(Cl)cc4Cl)n(-c4ccc(Cl)cc4)c3CCCNS(C)(=O)=O)CC2)CC1] | 1'-{[1-(4-chlorophenyl)-5-(2,4-dichlorophenyl)-2-{3-[(methylsulphonyl)amino]propyl}-1H-pyrrol-3-yl]carbonyl}-4,4-dimethyl-1,4'-bipiperidine-4'-carboxamide |
| 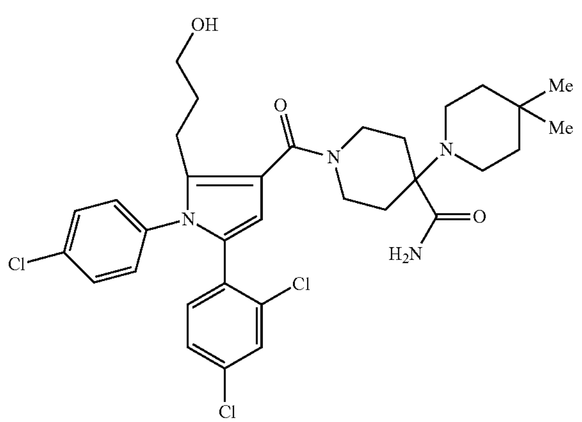 [SMILES: CC1(C)CCN(C2(C(N)=O)CCN(C(=O)c3cc(-c4ccc(Cl)cc4Cl)n(-c4ccc(Cl)cc4)c3CCCO)CC2)CC1] | 1'-{[1-(4-chlorophenyl)-5-(2,4-dichlorophenyl)-2-(3-hydroxypropyl)-1H-pyrrol-3-yl]carbonyl}-4,4-dimethyl-1,4'-bipiperidine-4'-carboxamide |

| Chemical structure | IUPAC name (ACDName) |
|---|---|
| 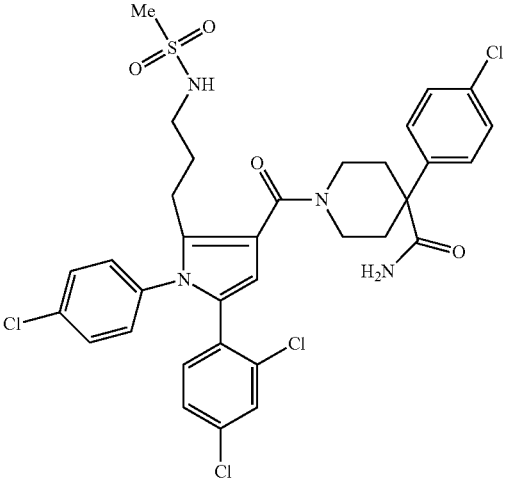 [SMILES: CS(=O)(=O)NCCCc1c(C(=O)N2CCC(C(N)=O)(c3ccc(Cl)cc3)CC2)cc(-c2ccc(Cl)cc2Cl)n1-c1ccc(Cl)cc1] | 4-(4-chlorophenyl)-1-{[1-(4-chlorophenyl)-5-(2,4-dichlorophenyl)-2-{3-[(methylsulphonyl)amino]propyl}-1H-pyrrol-3-yl]carbonyl}piperidine-4-carboxamide |
| 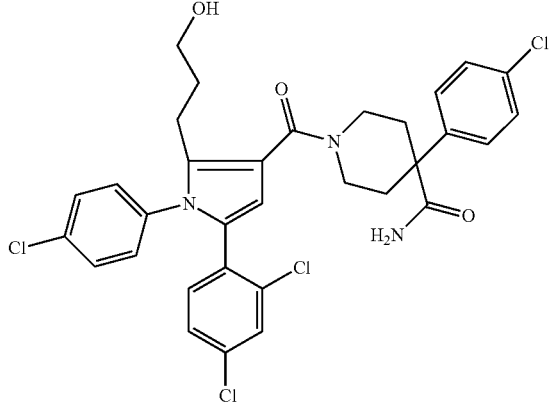 [SMILES: NC(=O)C1(c2ccc(Cl)cc2)CCN(C(=O)c2cc(-c3ccc(Cl)cc3Cl)n(-c3ccc(Cl)cc3)c2CCCO)CC1] | 4-(4-chlorophenyl)-1-{[1-(4-chlorophenyl)-5-(2,4-dichlorophenyl)-2-(3-hydroxypropyl)-1H-pyrrol-3-yl]carbonyl}piperidine-4-carboxamide |
| 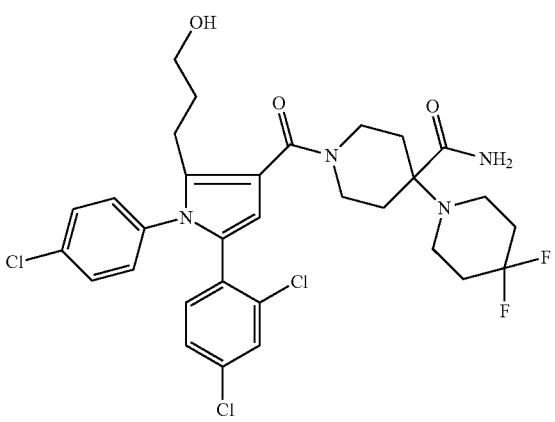 [SMILES: NC(=O)C1(N2CCC(F)(F)CC2)CCN(C(=O)c2cc(-c3ccc(Cl)cc3Cl)n(-c3ccc(Cl)cc3)c2CCCO)CC1] | 1'-{[1-(4-chlorophenyl)-5-(2,4-dichlorophenyl)-2-(3-hydroxypropyl)-1H-pyrrol-3-yl]carbonyl}-4,4-difluoro-1,4'-bipiperidine-4'-carboxamide |

| Chemical structure | IUPAC name (ACDName) |
| --- | --- |
| 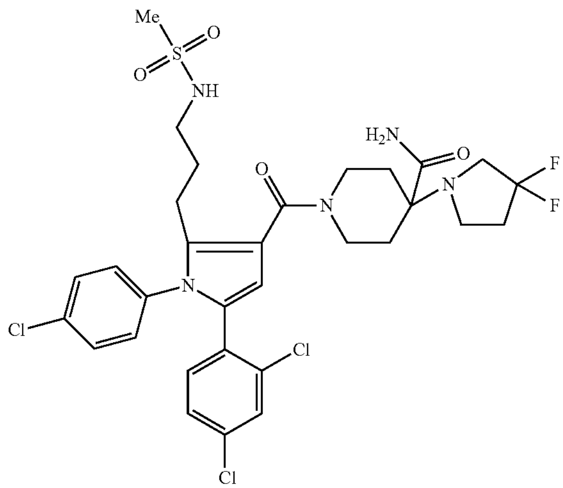 [SMILES: CS(=O)(=O)NCCCc1c(C(=O)N2CCC(C(N)=O)(N3CCC(F)(F)C3)CC2)cc(-c2ccc(Cl)cc2Cl)n1-c1ccc(Cl)cc1] | 1-{[1-(4-chlorophenyl)-5-(2,4-dichlorophenyl)-2-{3-[(methylsulphonyl)amino]propyl}-1H-pyrrol-3-yl]carbonyl}-4-(3,3-difluoropyrrolidin-1-yl)piperidine-4-carboxamide |
| 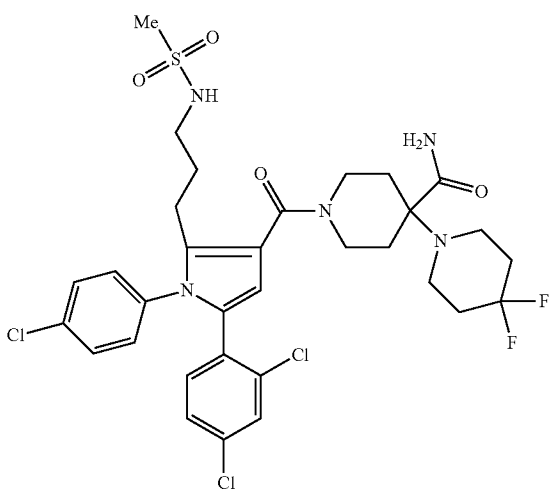 [SMILES: CS(=O)(=O)NCCCc1c(C(=O)N2CCC(C(N)=O)(N3CCC(F)(F)CC3)CC2)cc(-c2ccc(Cl)cc2Cl)n1-c1ccc(Cl)cc1] | 1'-{[1-(4-chlorophenyl)-5-(2,4-dichlorophenyl)-2-{3-[(methylsulphonyl)amino]propyl}-1H-pyrrol-3-yl]carbonyl}-4,4-difluoro-1,4'-bipiperidine-4'-carboxamide |
| 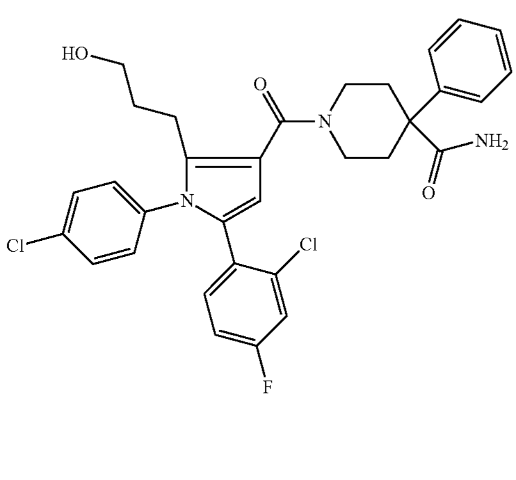 [SMILES: NC(=O)C1(c2ccccc2)CCN(C(=O)c2cc(-c3ccc(F)cc3Cl)n(-c3ccc(Cl)cc3)c2CCCO)CC1] | 1-{[5-(2-chloro-4-fluorophenyl)-1-(4-chlorophenyl)-2-(3-hydroxypropyl)-1H-pyrrol-3-yl]carbonyl}-4-phenylpiperidine-4-carboxamide |

| Chemical structure | IUPAC name (ACDName) |
|---|---|
| 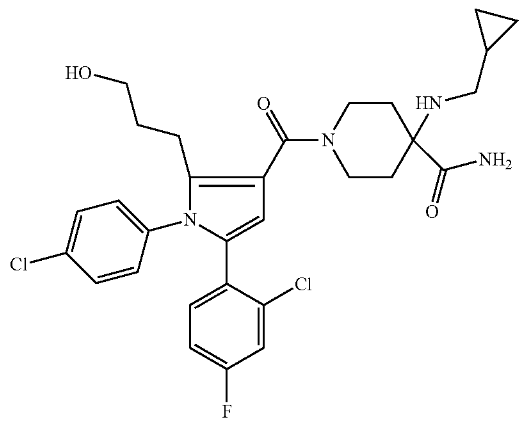 [SMILES: NC(=O)C1(NCC2CC2)CCN(C(=O)c2cc(-c3ccc(F)cc3Cl)n(-c3ccc(Cl)cc3)c2CCCO)CC1] | 1-{[5-(2-chloro-4-fluorophenyl)-1-(4-chlorophenyl)-2-(3-hydroxypropyl)-1H-pyrrol-3-yl]carbonyl}-4-[(cyclopropylmethyl)amino]piperidine-4-carboxamide |
| 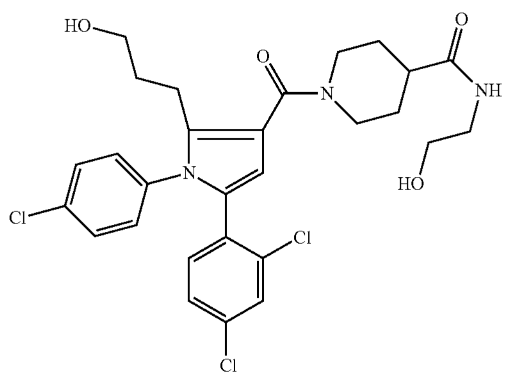 [SMILES: O=C(NCCO)C1CCN(C(=O)c2cc(-c3ccc(Cl)cc3Cl)n(-c3ccc(Cl)cc3)c2CCCO)CC1] | 1-{[5-(2-chloro-4-fluorophenyl)-1-(4-chlorophenyl)-2-(3-hydroxypropyl)-1H-pyrrol-3-yl]carbonyl}-N-(2-hydroxyethyl)piperidine-4-carboxamide |
| 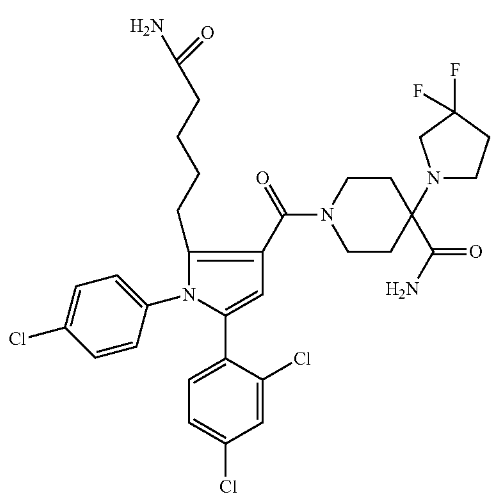 [SMILES: NC(=O)CCCCc1c(C(=O)N2CCC(C(N)=O)(N3CCC(F)(F)C3)CC2)cc(-c2ccc(Cl)cc2Cl)n1-c1ccc(Cl)cc1] | 1-{[2-(5-amino-5-oxopentyl)-1-(4-chlorophenyl)-5-(2,4-dichlorophenyl)-1H-pyrrol-3-yl]carbonyl}-4-(3,3-difluoropyrrolidin-1-yl)piperidine-4-carboxamide |

| Chemical structure | IUPAC name (ACDName) |
|---|---|
| 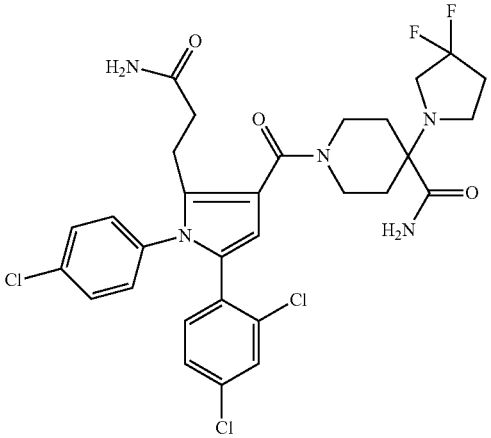 [SMILES: NC(=O)CCc1c(C(=O)N2CCC(C(N)=O)(N3CCC(F)(F)C3)CC2)cc(-c2ccc(Cl)cc2Cl)n1-c1ccc(Cl)cc1] | 1-{[2-(3-amino-3-oxopropyl)-1-(4-chlorophenyl)-5-(2,4-dichlorophenyl)-1H-pyrrol-3-yl]carbonyl}-4-(3,3-difluoropyrrolidin-1-yl)piperidine-4-carboxamide |
| 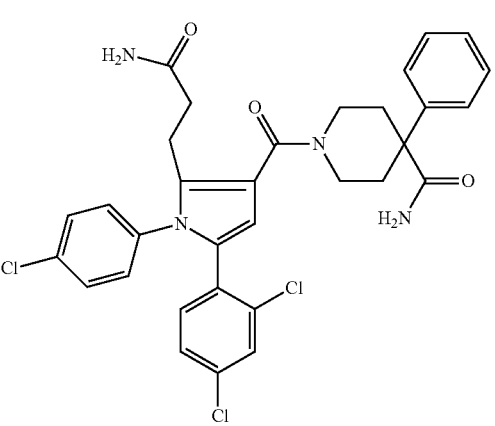 [SMILES: NC(=O)CCc1c(C(=O)N2CCC(C(N)=O)(c3ccccc3)CC2)cc(-c2ccc(Cl)cc2Cl)n1-c1ccc(Cl)cc1] | 1-{[2-(3-amino-3-oxopropyl)-1-(4-chlorophenyl)-5-(2,4-dichlorophenyl)-1H-pyrrol-3-yl]carbonyl}-4-phenylpiperidine-4-carboxamide |
| 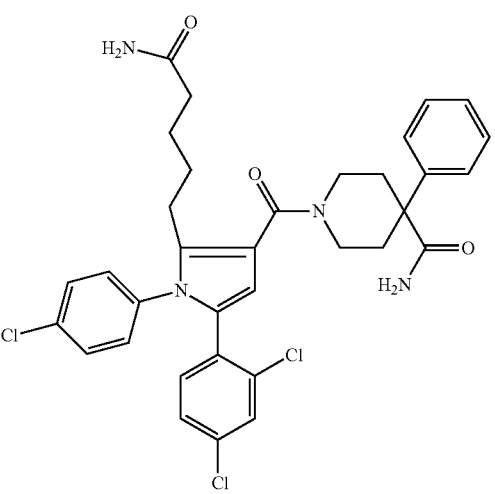 [SMILES: NC(=O)CCCCc1c(C(=O)N2CCC(C(N)=O)(c3ccccc3)CC2)cc(-c2ccc(Cl)cc2Cl)n1-c1ccc(Cl)cc1] | 1-{[2-(5-amino-5-oxopentyl)-1-(4-chlorophenyl)-5-(2,4-dichlorophenyl)-1H-pyrrol-3-yl]carbonyl}-4-phenylpiperidine-4-carboxamide |

| Chemical structure | IUPAC name (ACDName) |
|---|---|
| 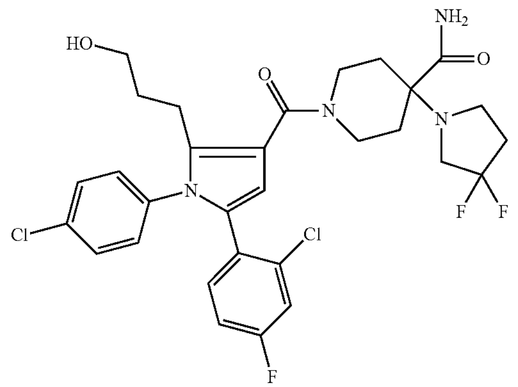 [SMILES: NC(=O)C1(N2CCC(F)(F)C2)CCN(C(=O)c2cc(-c3ccc(F)cc3Cl)n(-c3ccc(Cl)cc3)c2CCCO)CC1] | 1-{[5-(2-chloro-4-fluorophenyl)-1-(4-chlorophenyl)-2-(3-hydroxypropyl)-1H-pyrrol-3-yl]carbonyl}-4-(3,3-difluoropyrrolidin-1-yl)piperidine-4-carboxamide |
| 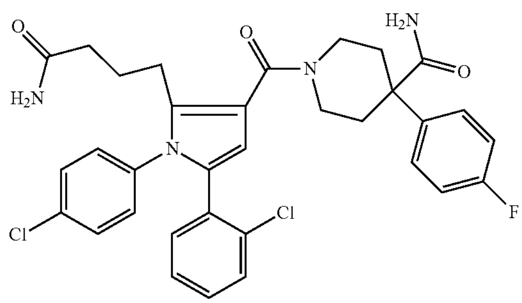 [SMILES: NC(=O)CCCc1c(C(=O)N2CCC(C(N)=O)(c3ccc(F)cc3)CC2)cc(-c2ccccc2Cl)n1-c1ccc(Cl)cc1] | 1-{[2-(4-amino-4-oxobutyl)-5-(2-chlorophenyl)-1-(4-chlorophenyl)-1H-pyrrol-3-yl]carbonyl}-4-(4-fluorophenyl)piperidine-4-carboxamide |
| 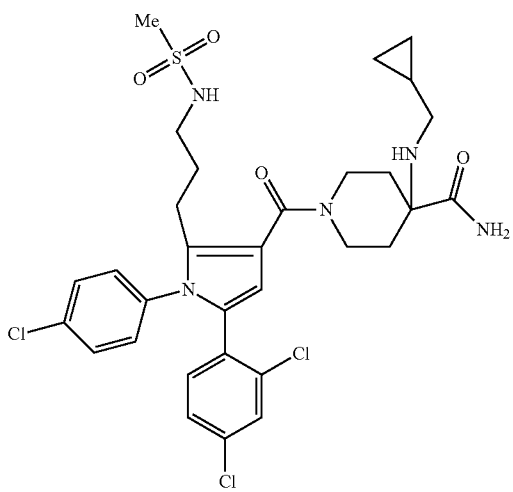 [SMILES: CS(=O)(=O)NCCCc1c(C(=O)N2CCC(NCC3CC3)(C(N)=O)CC2)cc(-c2ccc(Cl)cc2Cl)n1-c1ccc(Cl)cc1] | 1-{[1-(4-chlorophenyl)-5-(2,4-dichlorophenyl)-2-{3-[(methylsulphonyl)amino]propyl}-1H-pyrrol-3-yl]carbonyl}-4-[(cyclopropylmethyl)amino]piperidine-4-carboxamide |
| 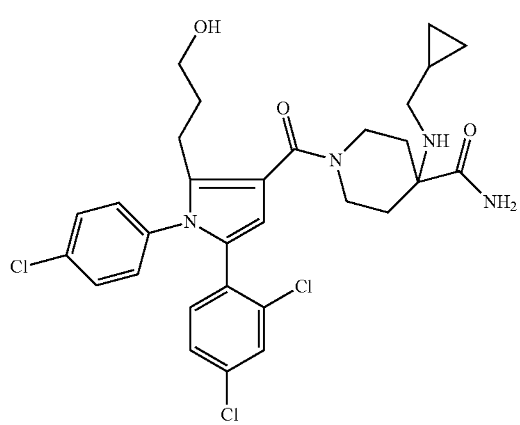 [SMILES: NC(=O)C1(NCC2CC2)CCN(C(=O)c2cc(-c3ccc(Cl)cc3Cl)n(-c3ccc(Cl)cc3)c2CCCO)CC1] | 1-{[1-(4-chlorophenyl)-5-(2,4-dichlorophenyl)-2-(3-hydroxypropyl)-1H-pyrrol-3-yl]carbonyl}-4-[(cyclopropylmethyl)amino]piperidine-4-carboxamide |

| Chemical structure | IUPAC name (ACDName) |
|---|---|
| 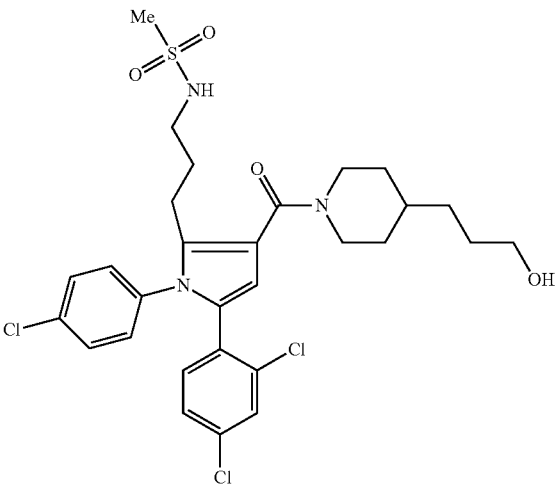 [SMILES: CS(=O)(=O)NCCCc1c(C(=O)N2CCC(CCCO)CC2)cc(-c2ccc(Cl)cc2Cl)n1-c1ccc(Cl)cc1] | N-{3-[1-(4-chlorophenyl)-5-(2,4-dichlorophenyl)-3-{[4-(3-hydroxypropyl)piperidin-1-yl]carbonyl}-1H-pyrrol-2-yl]propyl}methanesulphonamide |
| 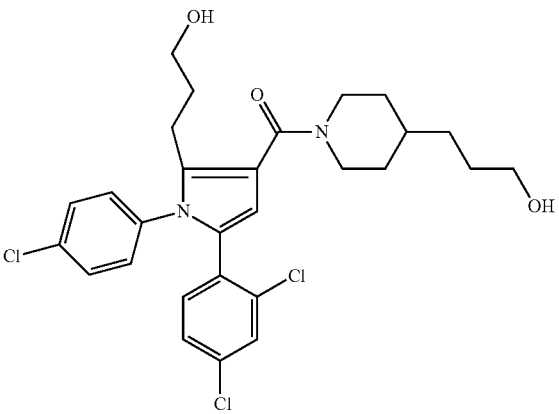 [SMILES: O=C(c1cc(-c2ccc(Cl)cc2Cl)n(-c2ccc(Cl)cc2)c1CCCO)N1CCC(CCCO)CC1] | 3-[1-(4-chlorophenyl)-5-(2,4-dichlorophenyl)-3-{[4-(3-hydroxypropyl)piperidin-1-yl]carbonyl}-1H-pyrrol-2-yl]propan-1-ol |
| 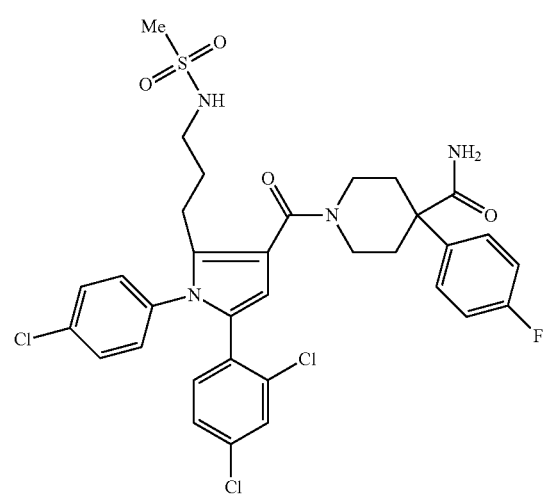 [SMILES: CS(=O)(=O)NCCCc1c(C(=O)N2CCC(C(N)=O)(c3ccc(F)cc3)CC2)cc(-c2ccc(Cl)cc2Cl)n1-c1ccc(Cl)cc1] | 1-{[1-(4-chlorophenyl)-5-(2,4-dichlorophenyl)-2-{3-[(methylsulphonyl)amino]propyl}-1H-pyrrol-3-yl]carbonyl}-4-(4-fluorophenyl)piperidine-4-carboxamide |

-continued

| Chemical structure | IUPAC name (ACDName) |
|---|---|
| 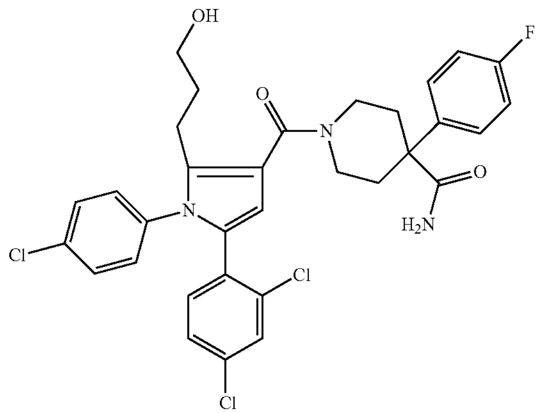 [SMILES: NC(=O)C1(c2ccc(F)cc2)CCN(C(=O)c2cc(-c3ccc(Cl)cc3Cl)n(-c3ccc(Cl)cc3)c2CCCO)CC1] | 1-{[1-(4-chlorophenyl)-5-(2,4-dichlorophenyl)-2-(3-hydroxypropyl)-1H-pyrrol-3-yl]carbonyl}-4-(4-fluorophenyl)piperidine-4-carboxamide |
| 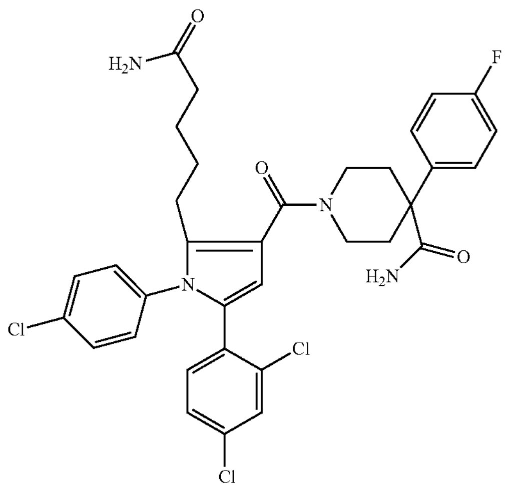 [SMILES: NC(=O)CCCCc1c(C(=O)N2CCC(C(N)=O)(c3ccc(F)cc3)CC2)cc(-c2ccc(Cl)cc2Cl)n1-c1ccc(Cl)cc1] | 1-{[2-(5-amino-5-oxopentyl)-1-(4-chlorophenyl)-5-(2,4-dichlorophenyl)-1H-pyrrol-3-yl]carbonyl}-4-(4-fluorophenyl)piperidine-4-carboxamide |
| 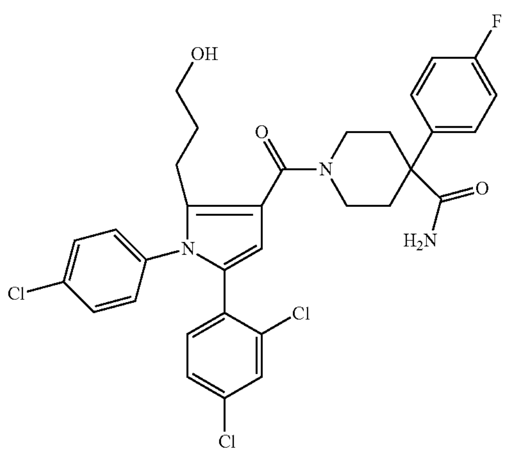 [SMILES: NC(=O)C1(c2ccc(F)cc2)CCN(C(=O)c2cc(-c3ccc(Cl)cc3Cl)n(-c3ccc(Cl)cc3)c2CCCO)CC1] | 1-{[5-(2-chloro-4-fluorophenyl)-1-(4-chlorophenyl)-2-(3-hydroxypropyl)-1H-pyrrol-3-yl]carbonyl}-4-(4-fluorophenyl)piperidine-4-carboxamide |

Among the compounds listed above, preference is given to:

1-{[1-(4-chlorophenyl)-5-(2,4-dichlorophenyl)-2-(4-hydroxybutyl)-1H-pyrrol-3-yl]carbonyl}-4-phenylpiperidine-4-carboxamide;

1-{[1-(4-chlorophenyl)-5-(2,4-dichlorophenyl)-2-(2-hydroxyethyl)-1H-pyrrol-3-yl]carbonyl}-4-phenylpiperidine-4-carboxamide;

1'-{[1-(4-chlorophenyl)-5-(2,4-dichlorophenyl)-2-(4-hydroxybutyl)-1H-pyrrol-3-yl]carbonyl}-4,4-difluoro-1,4'-bipiperidine-4'-carboxamide;

4-(4-chlorophenyl)-1-{[1-(4-chlorophenyl)-5-(2,4-dichlorophenyl)-2-(3-hydroxy propyl)-1H-pyrrol-3-yl]carbonyl}piperidine-4-carboxamide;

and their salts.

The subject of the present invention is also a method for preparing the compounds according to the invention.

This method is characterized in that the acid of formula (II) or a functional derivative of this acid of formula

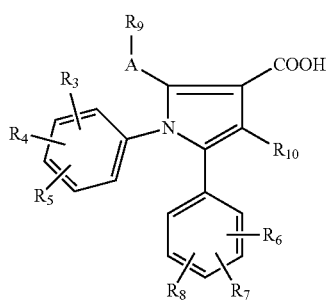

(II)

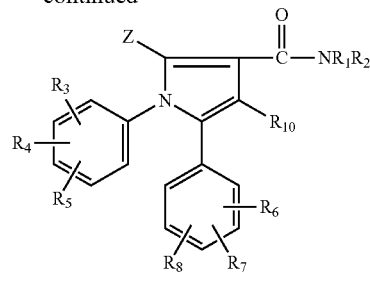

(Ia)

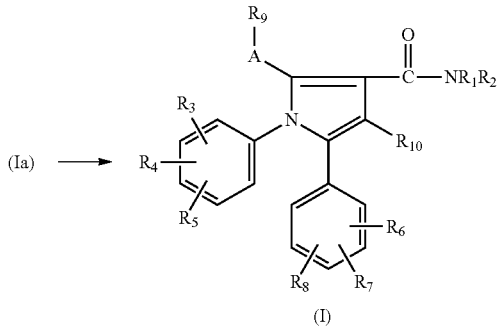

(I)

in which $R_3$, $R_4$, $R_5$, $R_6$, $R_7$, $R_9$, $R_{10}$ and A-$R_9$ are as defined for (I), is treated with an amine of formula $HNR_1R_2$ in which $R_1$ and $R_2$ are as defined for (I).

Optionally, the compound thus obtained is converted to one of its salts.

As a functional derivative of the acid (II), use may be made of the acid chloride, the anhydride, a mixed anhydride, a $C_1$-$C_4$ alkyl ester in which the alkyl is straight or branched, a benzyl ester, an activated ester, for example the p-nitrophenyl ester, or the free acid opportunely activated, for example, with N,N-dicyclohexylcarbodiimide or with benzotriazol-1-yloxotris(dimethylamino)phosphonium hexafluorophosphate (BOP) or benzotriazol-1-yloxotris(pyrrolidino)phosphonium hexafluorophosphate (PyBOP) or N—[N-(dimethylamino)-1-1,2,3-triazolo[4,5-b]pyridin-1-ylmethylene]-N-methylmethanaminium N-oxide] hexafluorophosphate (HBTU). These functional derivatives of the acid (II) correspond to the compounds (IIbis).

Thus, in the method according to the invention, it is possible to cause the acid chloride, obtained by the reaction of thionyl chloride with the acid of formula (II), to react with an amine $HNR_1R_2$, in an inert solvent, such as a chlorinated solvent (dichloromethane, dichloroethane, chloroform for example), an ether (tetrahydrofuran, dioxane for example), or an amide (N,N-dimethylformamide for example) under an inert atmosphere, at a temperature between 0° C. and room temperature, in the presence of a tertiary amine such as triethylamine, N-methylmorpholine or pyridine.

One variant consists in preparing the mixed anhydride of the acid of formula (II) by reacting ethyl chloroformate with the acid of formula (II), in the presence of a base such as triethylamine, and to cause it to react with an amine $HNR_1R_2$, in a solvent such as dichloromethane, under an inert atmosphere, at room temperature, in the presence of a base such as triethylamine.

Alternatively, the compounds of formulae (I) may be prepared according to the procedure of scheme 1 below.

According to scheme 1, the acid of formula (IIa) or one of its functional derivatives in which Z represents a group which is a chemical precursor of the group A-$R_9$ is treated with an amine of formula $HNR_1R_2$ as defined above in order to obtain an amide of formula (Ia).

Next, the group Z of the compound of formula (Ia) thus obtained is converted to a group A-$R_9$ by a method known to a person skilled in the art in order to obtain the product of formula (I).

By way of examples, the compounds of formula (I) in which $R_9$ corresponds to $NHSO_2Alk$, may be synthesized from the derivatives (IIa) in which Z corresponds to A-$OCH_2Ph$ by reacting with an amine $HNR_1R_2$, followed by debenzylation as described in step (d2) of scheme 2 below, and application of the reaction sequence described in scheme 4 below.

The compounds of formula (I) obtained by the various procedures may be subsequently separated from the reaction medium and purified according to conventional methods, for example by crystallization or chromatography.

The compounds of formula (II) and their precursors may be prepared according to scheme 2 below:

SCHEME 1

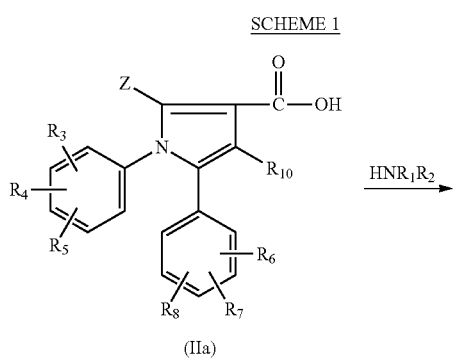

SCHEME 2

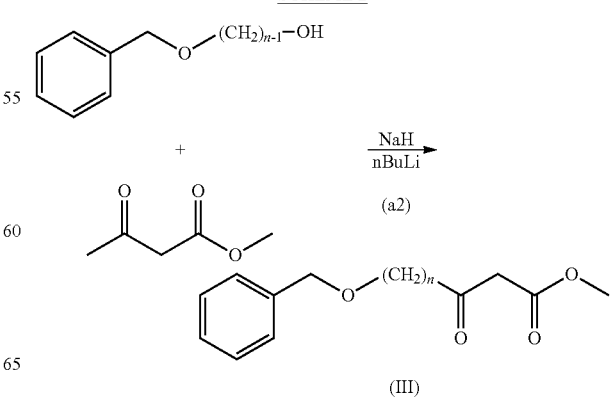

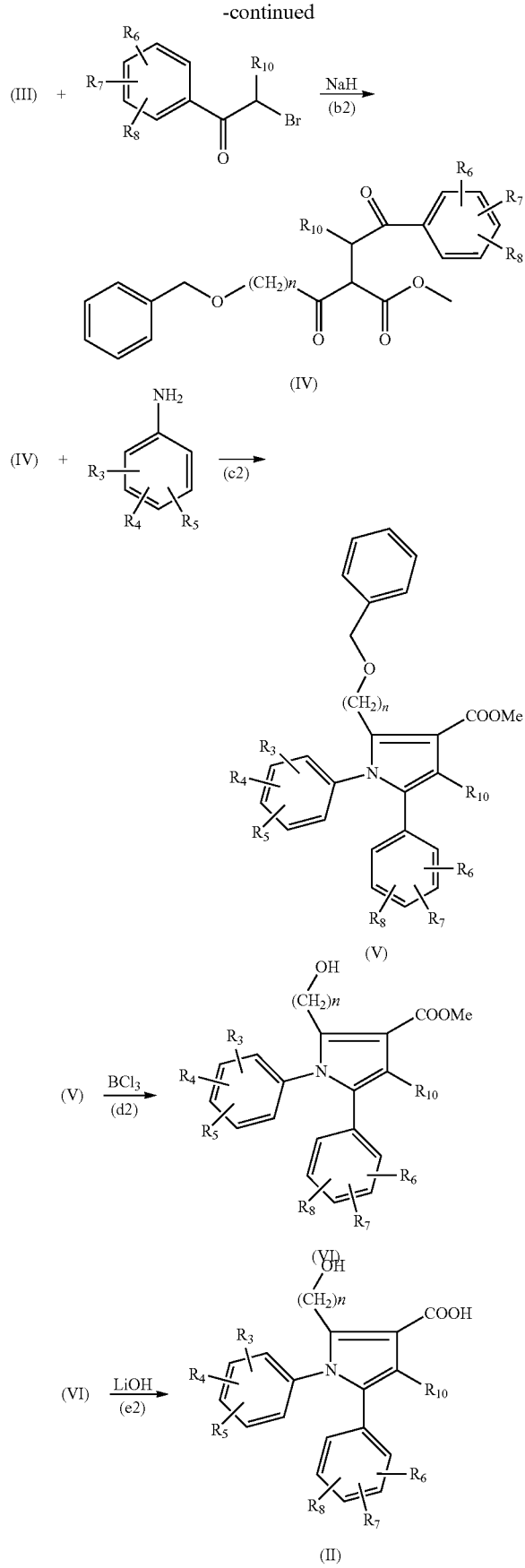

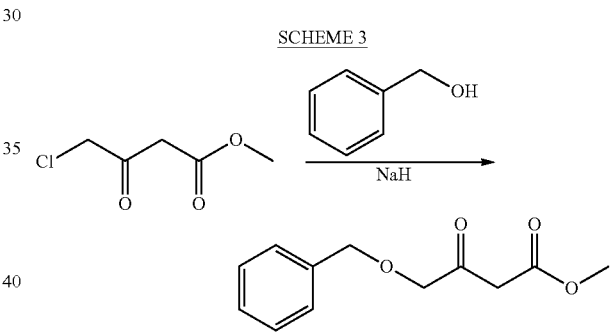

Step (a2) is a regioselective alkylation of methyl acetoacetate according to the procedure described in particular in JACS 96(4) 1974, page 1082 to 1087.

Step (b2) is an alkylation of compound (III) with a bromoacetophenone, in the presence of NaH.

Step (c2) is a cyclization of the diketone (III) with a substituted aniline (Paal-Knorr reaction). This cyclization is conventionally carried out in a solvent such as toluene under reflux in the presence of para-toluenesulphonic acid, or in acetic acid. It is also possible to carry out this cyclization with better yields in the presence of catalysts such as Montmorillonite K10 and in a microwave oven, as described in Adv. Synth. Catal. 2006, 348, 2191-2196.

Step (d2) is a benzyl ether deprotection which may be carried out for example with the aid of $BBr_3$ or $BCl_3$ in dichloromethane.

The alcohol (VI) obtained is then saponified, preferably with LiOH, at 70° C. in a methanol-water mixture.

The acid (II) thus obtained is treated with the amine $HN-R_1R_2$ to form the product (I) of the invention.

According to the various values of the group A, it is possible to use various methods, known to a person skilled in the art, to prepare the compounds of formula (II) and the compounds of formula (I) according to the invention.

In particular, when A corresponds to —$CH_2$—, the synthesis of the compound (III) is carried out by treating methyl 4-chloroacetoacetate with benzyl alcohol in the presence of NaH as described in scheme 3 below:

SCHEME 3

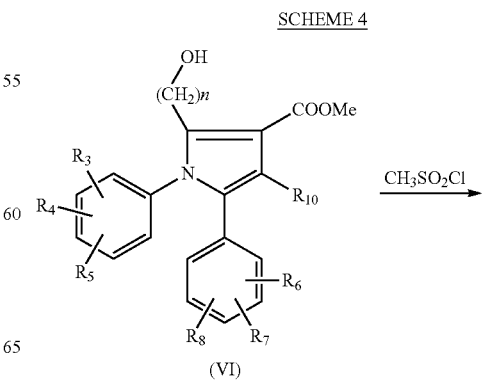

According to the various values of the $R_9$ group, it is possible to use various methods, known to a person skilled in the art, to prepare the compounds of formula (II) and the compounds of formula (I) according to the invention.

Thus, when a compound of formula (I) is prepared in which $A-R_9$ represents the group —$(CH_2)_3NHSO_2Alk$, it is possible to carry out the procedure as according to scheme 4 below:

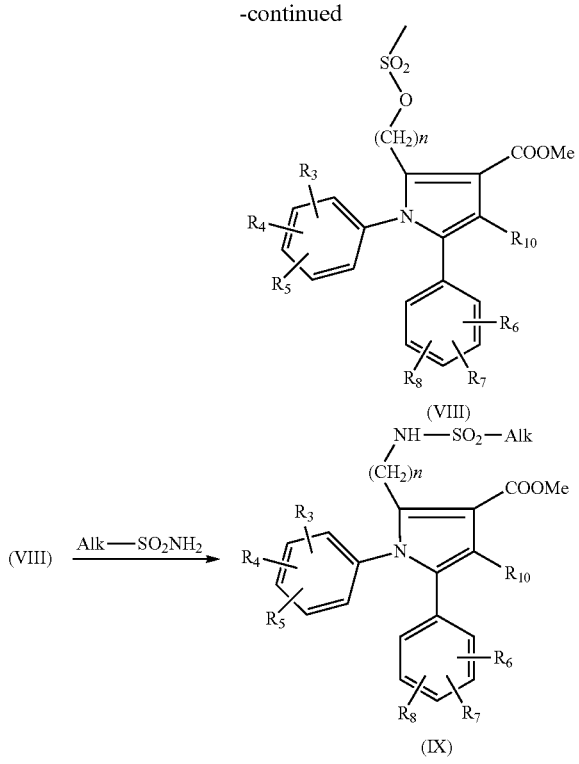

(VIII)

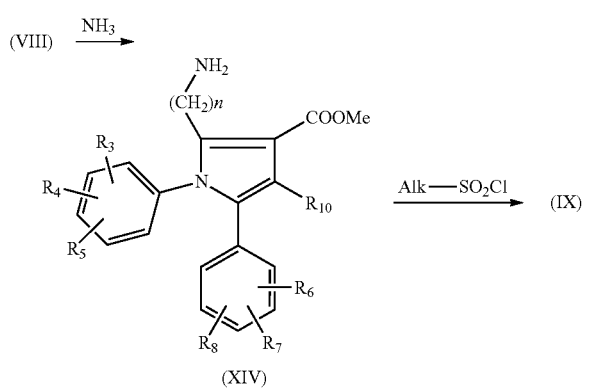

In this method, the alcohol (VI) is converted to a compound with a mesylate group (VIII) which is then treated with the sulphonamide $H_2NSO_2Alk$ in order to obtain the alkylsulphonamide derivative (IX).

One variant consists in carrying out the procedure according to scheme 5 below by converting the compound with the mesylate group (VIII) to an amine, and then treating the latter with a compound of the $AlkSO_2Cl$ type in order to obtain the ester (IX). The conversion of the alcohol (VI) to an amine (XIV) may be carried out by various methods known to a person skilled in the art, such as for example the Mitsunobu method.

The remainder of the synthesis is carried out by saponifying the ester (IX) and by coupling the acid obtained with the appropriate amine, as described in the general scheme 2.

In the case where the group $R_9$ represents COOH, the synthesis may be carried out according to scheme 6 below by oxidizing the compound (VI) to an acid with the aid of an oxidizing agent such as $CrO_3$, the acid obtained being protected with a t-butyl ester group. The methyl ester of the compound (XI) is saponified in order to obtain the acid (XII), which is then coupled with the amine $HNR_1R_2$ in order to obtain the ester (XIII) which is finally deprotected to give the compound according to the invention (I).

It is also possible, where appropriate, to directly oxidize a compound of formula (I), $R_9$ being equal to OH, with chromium VI in order to obtain the desired acid. This acid may then be treated so as to obtain the $R_9$ groups whose definition is given in the general formula.

SCHEME 6

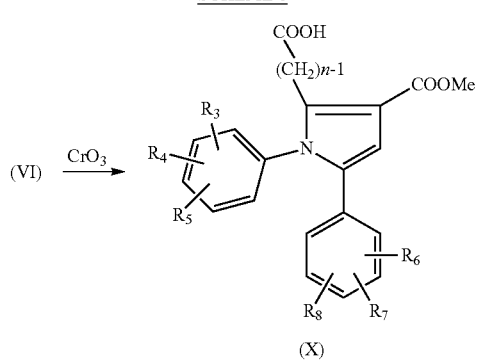

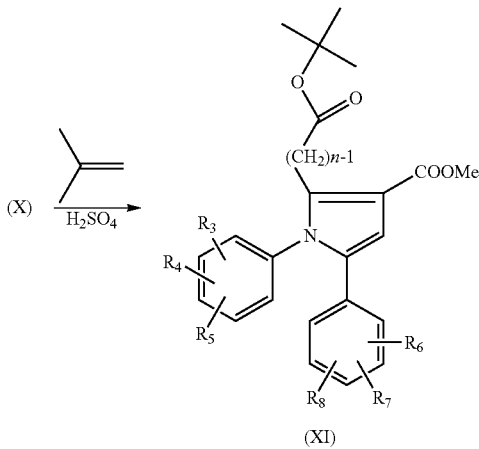

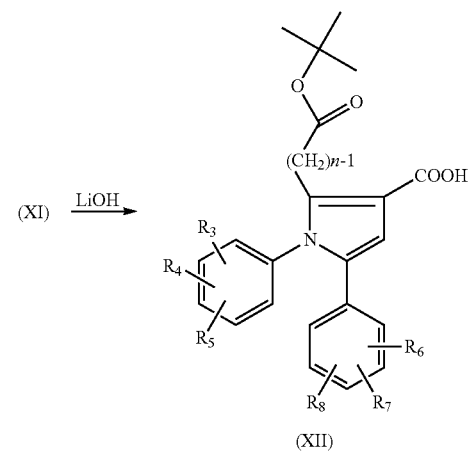

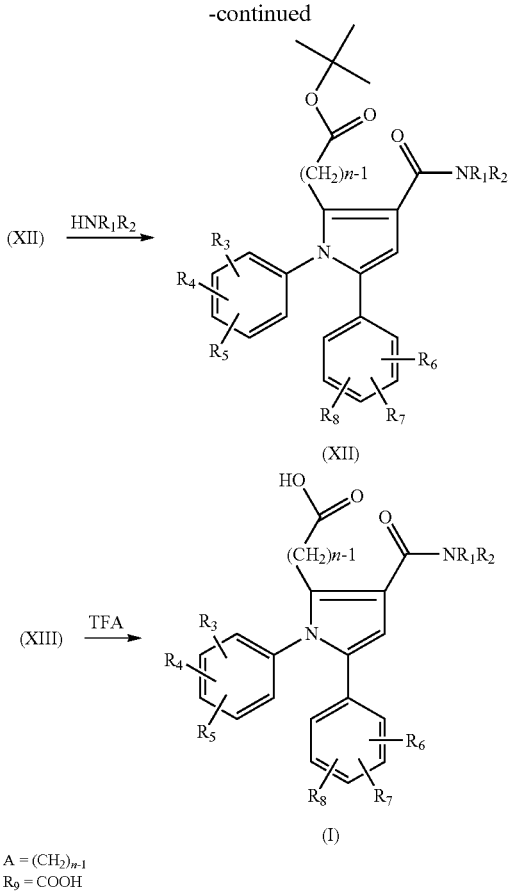

(XII)

(I)

with A = $(CH_2)_{n-1}$
$R_9$ = COOH

The amines of formula $HNR_1R_2$ are known or prepared by known methods, for example that described in J. Med. Chem.; 7; 1964; 619, 622.

The subject of the present invention is also the compounds of formula (II) and their functional derivatives (IIbis), used for the preparation of the compounds of formula (I). Among these compounds of formula (II) and (IIbis), those of formula (IIter) are differentiated in particular:

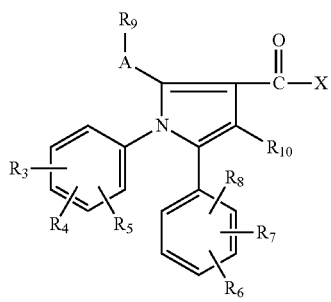

(IIter)

in which:
X represents a halogen atom, a hydroxyl, $(C_1-C_4)$alkoxyl or benzyloxy group;
and A, $R_3$, $R_4$, $R_5$, $R_6$, $R_7$, $R_3$ and $R_{10}$ are as defined for the compounds of formula (I).

More particularly, the subject of the present invention is the compounds of formula:

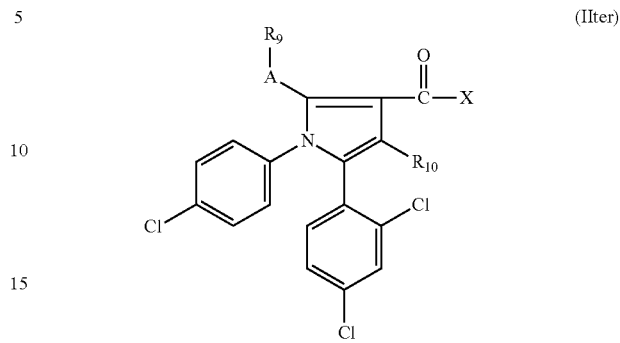

(IIter)

in which
X represents a halogen atom, a hydroxyl, $(C_1-C_4)$alkoxyl or benzyloxy group;
A represents a group —$(CH_2)_2$—, —$(CH_2)_3$—, —$(CH_2)_4$—, —$(CH_2)_5$—;
and $R_9$ represents a group —$OR_{12}$, —$NR_{12}R_{13}$, —$CONR_{12}R_{13}$, —$NR_{15}COR_{12}$
or
—$NR_{18}SO_2R_{14}$.

As regards the —$OR_{12}$ and —$NR_{12}R_{13}$ groups in the compounds of formula (IIter), preference is given more particularly to $R_{12}$ and $R_{13}$ which are different from hydrogen. More particularly, preference is given to $R_9$ which represents —OH, —$NHSO_2CH_3$, —$NHSO_2CF_3$, —O—$(CH_2)_2$—OH.

The following examples describe the preparation of some compounds in accordance with the invention. These examples are not limiting and merely illustrate the present invention. The numbers for the compounds exemplified refer to those given in the table below, which illustrates the chemical structures and the physical properties of some compounds according to the invention.

In the examples, the following abbreviations are used:
AcOEt: ethyl acetate
$BCl_3$: boron trichloride
DCM or $CH_2Cl_2$: dichloromethane
DIPEA: diisopropylethylamine
DMAP: dimethylaminopyridine
DMF: N,N-dimethylformamide.
HPLC: high-performance liquid chromatography
HBTU: N—[N-(dimethylamino)-1-1,2,3-triazolo[4,5-b]pyridin-1-ylmethylene]-N-methylmethanaminium N-oxide]hexafluorophosphate
HOBt: 1-hydroxybenzotriazole
$NaHCO_3$: sodium hydrogen carbonate
MeOH: methanol
PyBOP: benzotriazol-1-yloxotris(pyrrolidino)phosphonium hexafluorophosphate
RT: room temperature
TBTU: 2-(1H-benzotriazol-1-yl)-1,1,3,3-tetramethyluronium tetrafluoroborate
THF: tetrahydrofuran
HPLC: 'Ultra Performance' liquid chromatography The nuclear magnetic resonance spectra are recorded at 250 MHz or at 400 MHz in DMSO-d6. For the interpretation of the spectra, the following abbreviations are used:
s: singlet, t: triplet, u.c.: unresolved complex, bm: broad multiplet, mt: multiplet, bs: broad singlet, bd: broad doublet, d: doublet, dd: doublet of doublet, dt: doublet of triplet, bt: broad triplet, 2s: 2 singlet, q: quadruplet, quin: quintuplet.

The compounds according to the invention are analyzed by LC/UV/MS (liquid chromatography/UV detection/mass spectrometry) coupling. The characteristic molecular peak ($MH^+$, $MNa^+$, etc.) and the retention time (tr) in minutes (min) are measured.

Conditions A (HPLC)

Use is made of a Symmetry C18 column of 2.1×50 mm, 3.5 µm.

The eluent is made up as follows:
solvent A: 0.005% of trifluoroacetic acid (TFA) in water at pH 3.1;
solvent B: 0.005% of TFA in acetonitrile.
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C., flow rate 0.4 ml/minute.

The UV detection is carried out at λ=210 nM and the mass detection in positive ESI chemical ionization mode.

The UV detection is carried out with a diode array detector between 210 and 400 nm and the mass detection in positive ESI mode.

Conditions B (HPLC)

Use is made of an Xterra MS C18 column of 2.1×50 mm, 3.5 µm.

The eluent is made up as follows:
solvent A: 10 mM $AcONH_4$ at about pH 7
solvent B: acetonitrile
Gradient:

| Time (min) | % A | % B |
|---|---|---|
| 0 | 100 | 0 |
| 10 | 10 | 90 |
| 15 | 10 | 90 |
| 16 | 100 | 0 |
| 20 | 100 | 0 |

Column temperature: 30° C., flow rate: 0.4 ml/minute.
Detection: λ=220 nm

Conditions C (HPLC):

Use is made of an Acquity BEH C18 column (50×2.1 mm; 1.7 µm)

The eluent is made up as follows:
solvent A: 0.005% of TFA in water at about pH 3.1/acetonitrile (97/3)
solvent B: 0.035% of TFA in acetonitrile
Gradient:

| Time (min) | % A | % B |
|---|---|---|
| 0 | 100 | 0 |
| 2.3 | 5 | 95 |
| 2.9 | 5 | 95 |
| 3 | 100 | 0 |
| 3.5 | 100 | 0 |

Column temperature: 40° C., flow rate: 1 ml/minute.
Detection: λ=220 nm

Conditions D

Use is made of an Xterra MS C18 column of 2.1×50 mm, 3.5 µm.

The eluent is made up as follows:
solvent A: 0.005% of TFA in water at about pH 3.1/acetonitrile (97/3)
solvent B: acetonitrile
Gradient:

| Time (min) | % A | % B |
|---|---|---|
| 0 | 95 | 5 |
| 17 | 10 | 90 |
| 22 | 10 | 90 |

Column temperature: ambient, flow rate: 0.4 ml/minute.
Detection: λ=220 nm

Conditions E:

Use is made of an Acquity BEH C18 column of 2.1×50 mm; 1.7 µm)

The eluent is made up as follows:
solvent A: 0.05% of TFA in water at about pH 3.1/acetonitrile (97/3)
solvent B: 0.035% of TFA in acetonitrile.
Gradient:

| Time (min) | % A | % B |
|---|---|---|
| 0 | 99 | 1 |
| 2.3 | 5 | 95 |
| 2.9 | 5 | 95 |
| 3 | 99 | 1 |
| 3.5 | 99 | 1 |

Column temperature: 40° C., flow rate: 1 ml/minute.
Detection: λ=220 nm

PREPARATIONS

Preparation 1

5-(4-Chlorophenyl)-1-(2,4-dichlorophenyl)-2-(3-methanesulphonylaminopropyl)-1H-pyrrole-3-carboxylic acid 1A) Methyl ester of 6-benzyloxy-3-oxohexanoic acid (synthesis carried out based on: Angewandte Chemie (Int. Ed) 38(9), 1999, 1263-1266)

9.64 g of NaH are suspended in 300 ml of anhydrous THF. The suspension is cooled to 0° C. 20 g of methyl acetoacetate are added dropwise and the mixture is kept stirred for 45 minutes. The solution is then cooled to −20° C., and 96 ml of a 2.5 molar solution of n-BuLi in hexane are added. After stirring for 15 minutes, 51.8 g of benzyl 2-bromoethyl ether are added and the temperature is allowed to rise to 0° C. The solution is then neutralized with 200 ml of 1N HCl. The solution is diluted with 500 ml of ether, washed with $H_2O$, dried over $MgSO_4$, and evaporated. 50 g of an oil are obtained which, after chromatography (eluent cyclohexane/ethyl acetate), give 22.6 g of a colourless oil.

LCMS: M $Na^+$=273, tr=8.18.

1B) Methyl ester of 6-benzyloxy 2-2[2-(2,4-dichlorophenyl)-2-oxoethyl]-3-oxo-hexanoic acid 3.61 g of NaH are suspended in 500 ml of anhydrous THF. The mixture is cooled to 0° C. and 22.6 g of the compound of the preceding step 1A) diluted in 200 ml of THF are added dropwise. The mixture is kept stirred for 30 minutes and 24.1 g of 2,4-dichlorophenyl bromomethyl ketone dissolved in 100 ml of THF are added dropwise. The mixture is kept stirred for 3 hours at 0° C., and then for 17 hours at RT. The suspension is cooled to 0° C., and neutralized with 200 ml of N HCl. The mixture is extracted with ether, washed with H$_2$O, dried over MgSO$_4$, evaporated and chromatographed on 400 g of silica (eluent: cyclohexane/EtOAc). 25.7 g of the target compound are obtained.

LCMS: M=436 (2Cl), tr=11.01.

1C) Methyl ester of 2-(3-benzyloxypropyl)-1-(4-chlorophenyl)-5-(2,4-dichlorophenyl)-1H-pyrrole-3-carboxylic acid In a round-bottomed flask provided with a Dean-Stark condenser, 25.7 g of the compound obtained in the preceding step 1B) in 400 ml of toluene are heated under reflux for 3 days with 1 g of para-toluenesulphonic acid and 8.4 g of 4-chlorophenyl amine. The solution is then diluted with EtOAc, washed with saturated NaHCO$_3$, N HCl, dried over MgSO$_4$ and evaporated. The oil obtained is purified by chromatography on 400 g of silica (eluent cyclohexane/EtOAc gradient) to give 23.6 g of the desired compound.

LCMS: MNa$^+$=524.8 (3Cl) tr=9.95.

1D) Methyl ester of 1-(4-chlorophenyl)-5-(2,4-dichlorophenyl)-2-(3-hydroxypropyl)-1H-pyrrole-3-carboxylic acid 23.6 g of the compound obtained above in step 1C) are introduced into 300 ml of CH$_2$Cl$_2$. The mixture is cooled to −5° C. and a solution of 40 g of BCl$_3$ dimethyl sulphide in THF is added. The mixture is kept stirred for one hour, and then 70 ml of H$_2$O are added, the mixture is allowed to separate by settling, the organic phase is washed with H$_2$O, dried over MgSO$_4$, concentrated under vacuum and the product obtained is purified by chromatography on silica (eluent cyclohexane/EtOAc gradient). 15.6 g of the desired compound are obtained.

1E) Methyl ester of 1-(4-chlorophenyl)-5-(2,4-dichlorophenyl)-2-(3-methanesulphonyloxypropyl)-1H-pyrrole-3-carboxylic acid 0.5 g of the compound obtained in 1D) is introduced into 10 ml of CH$_2$Cl$_2$. 0.4 ml of DIPEA and 153 mg of DMAP are added. The mixture is cooled to −10° C. and 150 mg of mesyl chloride are added. The mixture is allowed to react for 2 hours at −10° C., washed with a solution of H$_2$O buffered to pH=2. The organic phase is dried over MgSO$_4$ and then evaporated. 0.59 g of the desired compound is obtained in the form of an oil.

LCMS: MH$^+$=516.1, tr=2.06.

1F) Methyl ester of 5-(4-chlorophenyl)-1-(2,4-dichlorophenyl)-2-(3-methane-sulphonylaminopropyl)-1H-pyrrole-3-carboxylic acid This step is carried out according to the information published in: Tetrahedron Letters 46 (2005) page 22159-2161.

18 mg of NaH are introduced into 10 ml of anhydrous DMF. The mixture is cooled to 0° C. and 42.7 mg of methyl sulphonamide are added and allowed to react for 15 minutes. A solution of 150 mg of the compound of the preceding step 1E) dissolved in 5 ml of anhydrous DMF is added. The mixture is allowed to return to RT and then the mixture is left for 3 hours at 60° C. The DMF is evaporated under vacuum, the residue is redissolved in CH$_2$Cl$_2$, washed with H$_2$O, dried over MgSO$_4$ and evaporated. 93 mg of the desired compound are obtained after chromatography (cyclohexane/EtOAc).

LCMS: MH+ (—OMe)=485.0, tr=1.96.

1G) 5-(4-chlorophenyl)-1-(2,4-dichlorophenyl)-2-(3-methanesulphonylaminopropyl)-1H-pyrrole-3-carboxylic acid 3.43 g of the product obtained in step 1F) are dissolved in 200 ml of methanol. 20 ml of water are added and the mixture is kept stirred for 17 hours at 65° C. The methanol is partially evaporated, and then the mixture is diluted with CH$_2$Cl$_2$ and acidified with concentrated HCl to pH=1 while cooling. The organic phase is dried over MgSO$_4$, filtered and evaporated, and 3.24 g (97%) of a white solid are obtained.

LCMS: MH+ (—OMe)=485.1, tr=1.74.

Preparation 2

1-(4-Chlorophenyl)-5-(2,4-dichlorophenyl)-2-hydroxymethyl-1H-pyrrole-3-carboxylic acid

2A) Methyl ester of 4-benzyloxy-3-oxobutyric acid 13.28 g of NaH are introduced into 200 ml of dry THF. The mixture is cooled to about 0° C. and then 25 g of methyl ester of 4-chloro-3-oxobutyric acid are added dropwise. 17 ml of benzyl alcohol are then added dropwise. The solution takes on a red colour. The mixture is kept stirred at RT for 17 hours and the reaction mixture is poured into 120 ml of 2N HCl. The mixture is extracted with ether. The organic phase is dried over MgSO$_4$ and evaporated. After chromatography (eluent: cyclohexane/EtOAc), 23.5 g of product are obtained.

2B) Methyl ester of 4-benzyloxy-2-[2-(2,4-dichlorophenyl)-2-oxoethyl]-3-oxobutyric acid 4.13 g of NaH are introduced into 500 ml of dry THF, cooled to 0° C. 23 g of the compound obtained in step 2A) are added dropwise. The mixture is kept stirred for 30 minutes, and then 27.7 g of 2,4-dichlorophenacyl bromide are added dropwise. The mixture is allowed to react for 3 hours at 0° C., and then the temperature is raised to RT for 17 hours. 150 ml of 2N HCl are added, after cooling, followed by extraction with ether, washing with H$_2$O, drying and evaporation. 26 g of product are obtained whose analysis by LCMS confirms the structure.

2C) Methyl ester of 2-benzyloxymethyl-1-(4-chlorophenyl)-5-(2,4-dichlorophenyl)-1H-pyrrole-3-carboxylic acid To a round-bottomed flask are added 3.8 g obtained in step 2B), 15 ml of CH$_2$Cl$_2$ and 4 g of Montmorillonite K10. The mixture is kept stirred under nitrogen for 72 hours. The mixture is filtered, rinsed with CH$_2$Cl$_2$, washed with dilute HCl, dried and the organic phase is evaporated. After chromatography, 3 g of the desired pyrrole are obtained.

2D) Methyl ester of 1-(4-chlorophenyl)-5-(2,4-dichlorophenyl)-2-hydroxymethyl-1H-pyrrole-3-carboxylic acid 8 g of the product of step 2C) in 150 ml of CH$_2$Cl$_2$ are dissolved in a round-bottomed flask. The mixture is cooled to 0° C. and 13 g of BCl$_3$-dimethyl sulphide complex dissolved beforehand in 50 ml of CH$_2$Cl$_2$ are added dropwise. After reacting for 1 hour, the mixture is neutralized with solid NaHCO$_3$ until the gaseous release ceases. The organic phase is dried, and 4.5 g of oil are obtained after chromatography whose NMR spectrum confirms the structure.

2E) 1-(4-Chlorophenyl)-5-(2,4-dichlorophenyl)-2-hydroxymethyl-1H-pyrrole-3-carboxylic acid 2.7 g of the compound of step 2D) are reacted with 1 g of LiOH in a mixture of dioxane and H$_2$O 90/10 for 17 hours at 60° C. After evaporation, the mixture is redissolved in CH$_2$Cl$_2$, washed with a solution pH=2, and purified by chromatography. 350 mg of the desired product are obtained whose structure is confirmed by LCMS and NMR.

EXAMPLES

Example 1

1-{[1-(4-Chlorophenyl)-5-(2,4-dichlorophenyl)-2-{3-[(methylsulphonyl)amino]propyl}-1H-pyrrol-3-yl]carbonyl}-4-phenyl-4-piperidinecarboxamide 0.5 g of the compound obtained in step 1G) of Preparation 1, 0.7 ml of DIPEA and 350 mg of 4-phenylpiperidine-4- carboxamide acid in 10 ml of CH$_2$Cl$_2$ are introduced into a round-bottomed flask under nitrogen. The mixture is cooled to 0° C. 3.25 g of TBTU are added and the mixture is kept stirred for 30 minutes. The mixture is washed with saturated NaHCO$_3$, buffer 2, and then with a saturated NaCl solution. The mixture is dried over MgSO$_4$, filtered and evaporated.

The crude product is chromatographed on silica (eluent CH$_2$Cl$_2$/MeOH) to give 0.48 g of the desired compound whose structure is confirmed by LCMS and NMR.

LC/MS (B): MH$^+$=687, tr=10.16.

Example 2

1'-[1-(4-Chlorophenyl)-5-(2,4-dichlorophenyl)-2-hydroxymethyl-1H-pyrrole-3-carbonyl]-[1,4']bipiperidinyl-4'-carboxamide There is dissolved 0.3 g of the product obtained in step 2E) of Preparation 2 in 20 ml of CH$_2$Cl$_2$, with 27 ml of DIPEA. 0.16 g of [1,4]bipiperidinyl-4'-carboxamide and 0.22 g of TBTU are then added. The mixture is kept stirred for 1 hour and then diluted with 50 ml of CH$_2$Cl$_2$, washed with a buffer solution pH=2, a saturated NaHCO$_3$ solution, the organic phase is dried and evaporated. 350 mg of the solid compound are obtained after chromatography whose structure is confirmed by LCMS and NMR.

Example 3

4-(4-Chlorophenyl)-1-{[1-(4-chlorophenyl)-5-(2,4-dichlorophenyl)-2-(3-hydroxypropyl)-1H-pyrrol-3-yl]carbonyl}piperidine-4-carboxamide 3a) 1-(4-Chlorophenyl)-5-(2,4-dichlorophenyl)-2-(3-hydroxypropyl)-1H-pyrrole-3-carboxylic acid In a round-bottomed flask under nitrogen, 5 g of the compound obtained in step 1D) of Preparation 1 are dissolved in 180 ml of water and 20 ml of methanol. 5 g of LiOH are added and the mixture is heated at 60° C. for 17 hours. The solvent is evaporated under vacuum and the residue obtained is redissolved in 100 ml of CH$_2$Cl$_2$ and 50 ml of water. After acidification with HCl to pH=1, drying of the organic phase with MgSO$_4$, filtration and then evaporation, 4.67 g of an acid compound are obtained.

3b) 4-(4-Chlorophenyl)-1-{[1-(4-chlorophenyl)-5-(2,4-dichlorophenyl)-2-(3-hydroxypropyl)-1H-pyrrol-3-yl]carbonyl}piperidine-4-carboxamide Into a round-bottomed flask under nitrogen are introduced 300 mg of the acid obtained in step 3a) in 30 ml of DMF, 246 mg of 4-(4-chlorophenyl)piperidine-4-carboxamide (prepared according to the procedure described in patent application US 2005/0070549, in particular in Example 460, paragraphs 1394 to 1397), 0.62 ml of DIPEA and 250 mg of TBTU.

The mixture is kept stirred for 17 hours at RT. The mixture is evaporated, taken up in CH$_2$Cl$_2$, washed with N HCl, dried over MgSO$_4$, filtered and evaporated.

The crude product is chromatographed on silica (eluent CH$_2$Cl$_2$/MeOH) to give 0.32 g of the desired compound whose structure is confirmed by LCMS and NMR.

Table 1 shows the chemical structures of some compounds according to the invention and their physical properties (analysis by LC/UV/MS coupling: liquid chromatography/UV detection/mass spectrometry). In this table, Me means methyl. The compounds listed are prepared according to the methods of preparation described above and in particular by following procedures similar to those described in Examples 1 to 3.

TABLE 1

| Compound | A-R$_9$ | NR$_1$R$_2$ | LC/MS characterization MH+; tr; (condition) |
|---|---|---|---|
| 1 | —(CH$_2$)$_3$—OH | | MH+ = 617<br>tr = 7.34<br>(A) |

TABLE 1-continued

[Structure: 1-(4-chlorophenyl)-2-(2,4-dichlorophenyl)-pyrrole-3-carboxamide core with substituents A-R9 at position 5, R10 at position 4, and NR1R2 on the carboxamide]

| Compound | A-R9 | NR1R2 | LC/MS characterization MH+; tr; (condition) |
|---|---|---|---|
| 2 | —(CH2)3—NHSO2CF3 | 1-methyl-4-(piperidin-1-yl)piperidine-4-carboxamide | MH+ = 694<br>tr = 1.42<br>(C) |
| 3 | —(CH2)3—NHSO2CF3 | 1-methyl-4-(piperidin-1-yl)piperidine-4-carboxamide | NH+ = 748<br>tr = 8.46<br>(A) |
| 4 | —(CH2)3—OH | 1-methyl-4-phenylpiperidine-4-carboxamide | MH+ = 610<br>tr = 7.5<br>(D) |
| 5 | —(CH2)3—N(pyrrolidine) | 1-methyl-4-phenylpiperidine-4-carboxamide | MH+ = 663<br>tr = 9.5<br>(B) |
| 6 | —(CH2)3—NHSO2Me | 1-methyl-4-phenylpiperidine-4-carboxamide | MH+ = 687<br>tr = 10.16<br>(A) |
| 7 | —(CH2)3—O—(CH2)2—OH | 1-methyl-4-(piperidin-1-yl)piperidine-4-carboxamide | MH+ = 661<br>tr = 7.36<br>(A) |

TABLE 1-continued
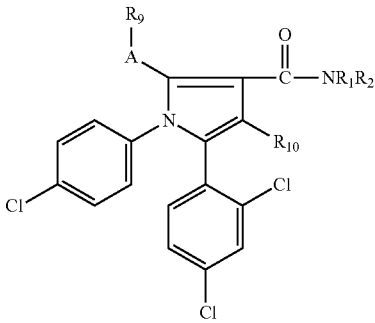
| Compound | A-R₉ | NR₁R₂ | LC/MS characterization MH+; tr; (condition) |
|---|---|---|---|
| 8 | —CH₂—OH | 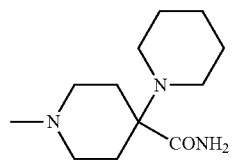 | MH+ = 589<br>tr = 1.36<br>(C) |
| 9 | —(CH₂)₄—OH | 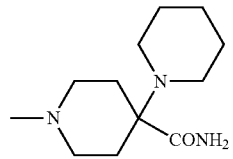 | MH+ = 631<br>tr = 1.41<br>(E) |
| 10 | —(CH₂)₄—OH | 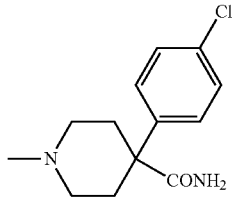 | MH+ = 658<br>tr = 1.88<br>(E) |
| 11 | —(CH₂)₂—OH | 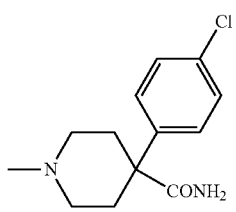 | MH+ = 630<br>tr = 1.87<br>(E) |
| 12 | —(CH₂)₂—OH | 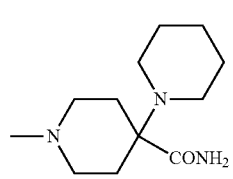 | MH+ = 603<br>tr = 1.36<br>(E) |
| 13 | —(CH₂)₄—OH | 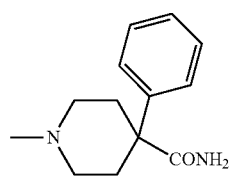 | MH+ = 624<br>tr = 1.77<br>(E) |

TABLE 1-continued

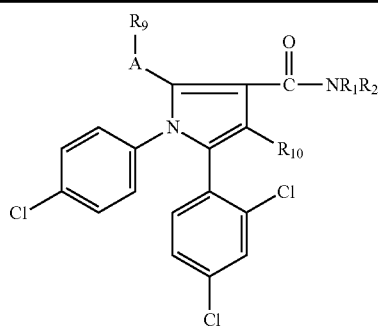

| Compound | A-R₉ | NR₁R₂ | LC/MS characterization MH+; tr; (condition) |
|---|---|---|---|
| 14 | —(CH₂)₂—OH | 1-methyl-4-phenylpiperidine-4-carboxamide | MH+ = 596<br>tr = 1.76<br>(E) |
| 15 | —(CH₂)₄—OH | 1-methyl-4-[(2,2,2-trifluoroethyl... NH—(CH₂)₂—CF₃; CONH₂ | MH+ = 659<br>tr = 1.49<br>(E) |
| 16 | —(CH₂)₂—OH | 1-methyl-4-[NH—(CH₂)₂—CF₃]; CONH₂ | MH+ = 631<br>tr = 1.44<br>(E) |
| 17 | —(CH₂)₄—OH | 1-methyl-4-(4,4-difluoropiperidin-1-yl)piperidine-4-carboxamide | MH+ = 667<br>tr = 1.61<br>(E) |
| 18 | —(CH₂)₂—OH | 1-methyl-4-(4,4-difluoropiperidin-1-yl)piperidine-4-carboxamide | MH+ = 639<br>tr = 1.58<br>(E) |
| 19 | —(CH₂)₄—OH | 1-methyl-4-(3,3-difluoropyrrolidin-1-yl)piperidine-4-carboxamide | MH+ = 653<br>tr = 1.73<br>(E) |
| 20 | —(CH₂)₂—OH | 1-methyl-4-(3,3-difluoropyrrolidin-1-yl)piperidine-4-carboxamide | MH+ = 625<br>tr = 1.71<br>(E) |

TABLE 1-continued
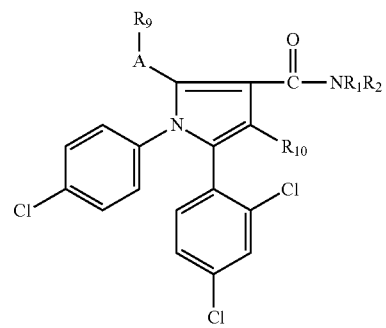
| Compound | A-R₉ | NR₁R₂ | LC/MS characterization MH+; tr; (condition) |
|---|---|---|---|
| 21 | —(CH₂)₄—OH | 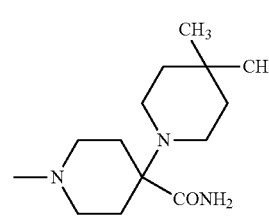 | MH+ = 659<br>tr = 1.48<br>(E) |
| 22 | —(CH₂)₂—OH | 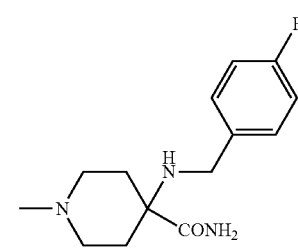 | MH+ = 643<br>tr = 1.44<br>(E) |
| 23 | —(CH₂)₄—OH | 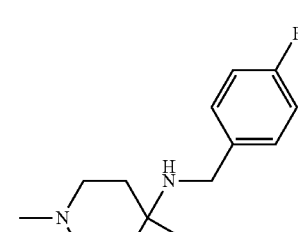 | MH+ = 671<br>tr = 1.49<br>(E) |
| 24 | —(CH₂)₂—OH | 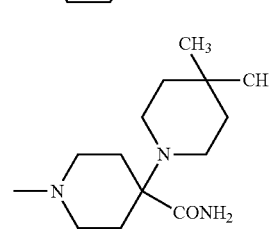 | MH+ = 631<br>tr = 1.43<br>(E) |
| 25 | —(CH₂)₄—OH | 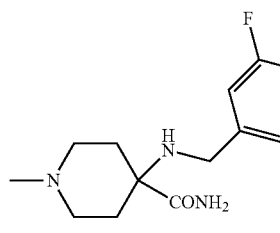 | MH+ = 671<br>tr = 1.51<br>(E) |

TABLE 1-continued
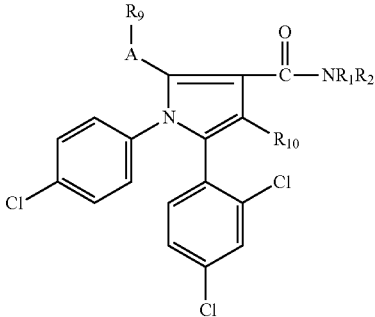
| Compound | A-R9 | NR1R2 | LC/MS characterization MH+; tr; (condition) |
|---|---|---|---|
| 26 | —(CH2)2—OH | 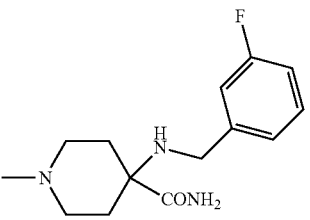 | MH+ = 643<br>tr = 1.46<br>(E) |
| 27 | —(CH2)3—NHSO2CH3 | 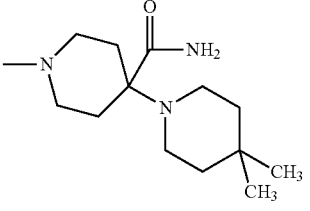 | |
| 28 | —(CH2)3—OH | 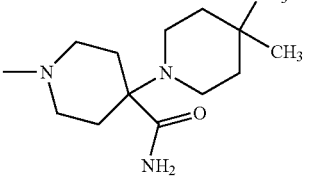 | |
| 29 | —(CH2)3—NHSO2CH3 | 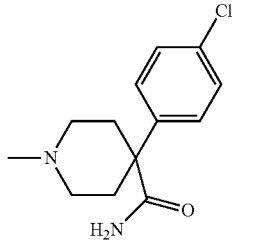 | MH+ = 721<br>tr = 1.94<br>(E) |
| 30 | —(CH2)3—OH | 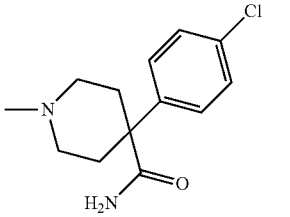 | MH+ = 644<br>tr = 1.94<br>(E) |

TABLE 1-continued

| Compound | A-R$_9$ | NR$_1$R$_2$ | LC/MS characterization MH+; tr; (condition) |
|---|---|---|---|
| 31 | —(CH$_2$)$_3$—OH | 1-methylpiperidine-4-carboxamide linked to 4,4-difluoropiperidine | MH+ = 653<br>tr = 1.66<br>(E) |
| 32 | —(CH$_2$)$_3$—NHSO$_2$CH$_3$ | 1-methylpiperidine-4-carboxamide linked to 3,3-difluoropyrrolidine | MH+ = 716<br>tr = 1.75<br>(E) |
| 33 | —(CH$_2$)$_3$—NHSO$_2$CH$_3$ | 1-methylpiperidine-4-carboxamide linked to 4,4-difluoropiperidine | MH+ = 730<br>tr = 1.64<br>(E) |
| 34 | —(CH$_2$)$_3$—OH | 1-methyl-4-phenylpiperidine-4-carboxamide | MH+ = 594<br>tr = 1.66<br>(E) |
| 35 | —(CH$_2$)$_3$—OH | 4-(cyclopropylmethylamino)-1-methylpiperidine-4-carboxamide | MH+ = 587<br>tr = 1.29<br>(E) |

TABLE 1-continued
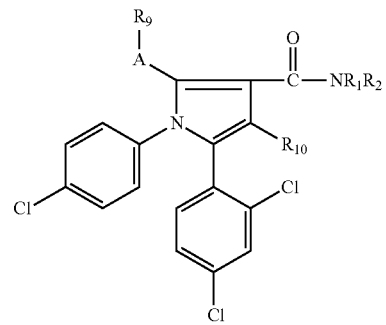
| Compound | A-R$_9$ | NR$_1$R$_2$ | LC/MS characterization MH+; tr; (condition) |
|---|---|---|---|
| 36 | —(CH$_2$)$_3$—OH | 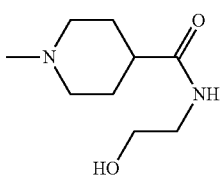 | MH+ = 562<br>tr = 1.37<br>(E) |
| 37 | —(CH$_2$)$_4$—CONH$_2$ | 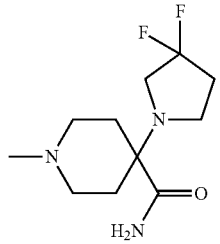 | MH+ = 680<br>tr = 1.65<br>(E) |
| 38 | —(CH$_2$)$_2$—CONH$_2$ | 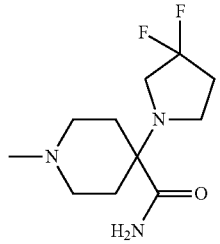 | MH+ = 652<br>tr = 1.59<br>(E) |
| 39 | —(CH$_2$)$_2$—CONH$_2$ | 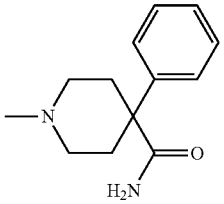 | MH+ = 623<br>tr = 1.64<br>(E) |
| 40 | —(CH$_2$)$_4$—CONH$_2$ | 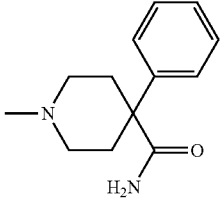 | NH+ = ?<br>tr = ?<br>(E) |

TABLE 1-continued
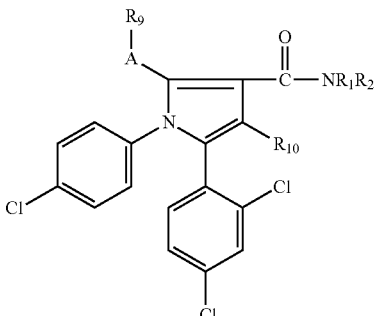
| Compound | A-R$_9$ | NR$_1$R$_2$ | LC/MS characterization MH+; tr; (condition) |
|---|---|---|---|
| 41 | —(CH$_2$)$_3$—OH | 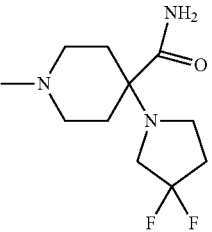 | MH+ = 624<br>tr = 1.64<br>(E) |
| 42 | —(CH$_2$)$_3$—CONH$_2$ | 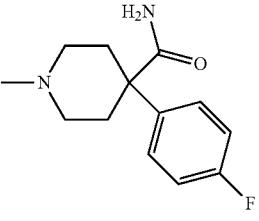 | MH+ = 621<br>tr = 1.55<br>(E) |
| 43 | —(CH$_2$)$_3$—NHSO$_2$Me | 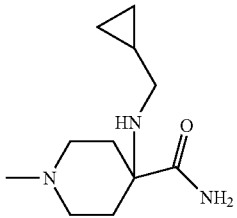 | MH+ = 680<br>tr = 1.4<br>(E) |
| 44 | —(CH$_2$)$_3$—OH | 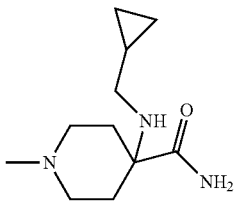 | MH+ = 603<br>tr = 1.39<br>(E) |
| 45 | —(CH$_2$)$_3$—NHSO$_2$Me | 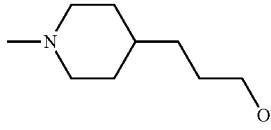 | MH+ = 626<br>tr = 1.81<br>(E) |
| 46 | —(CH$_2$)$_3$—OH | 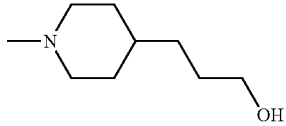 | MH+ = 549<br>tr = 1.8<br>(E) |

TABLE 1-continued

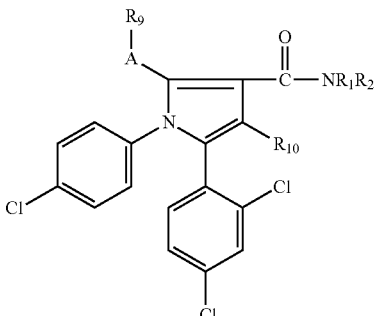

| Compound | A-R₉ | NR₁R₂ | LC/MS characterization MH+; tr; (condition) |
|---|---|---|---|
| 47 | —(CH₂)₃—NHSO₂Me | 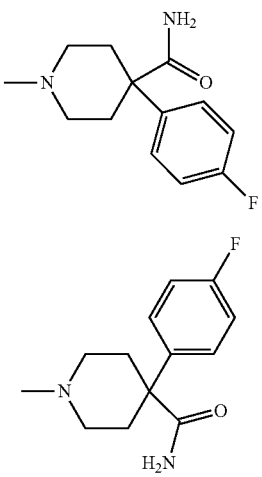 | MH+ = 705<br>tr = 1.83<br>(E) |
| 48 | —(CH₂)₃—OH | 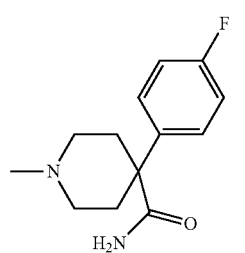 | MH+ = 628<br>tr = 1.81<br>(E) |
| 49 | —(CH₂)₄—CONH₂ | 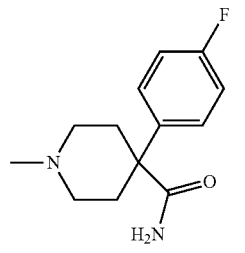 | MH+ = 669<br>tr = 1.72<br>(E) |
| 50 | —(CH₂)₃—OH | 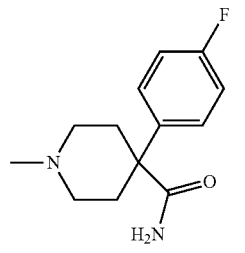 | MH+ = 612<br>tr = 1.69<br>(E) |

The analyses carried out by NMR for some compounds are given below:

Compound 1

¹H NMR: DMSO-d6 (250 MHz): δ (ppm): 1.20-1.99: u.c.: 10H, 2.52-3.02: u.c.: 8H, 3.17: t: 2H, 3.55: bd: 2H, 4.41: bd: 2H, 6.38: s: 1H, 7.22: d: 2H, 7.27-7.31: u.c.: 2H, 7.43: d: 2H, 7.53: d: 1H, 8.18: bs: 2H, 10.23: t: 1H.

Compound 2

¹H NMR: DMSO-d6 (400 MHz): δ (ppm): 1.30-1.58: u.c.: 8H, 1.73: mt: 2H, 1.88: bd: 2H, 2.45: bt: 4H, 2.62: t: 2H, 2.73: q: 2H, 2.78: s: 3H, 3.35: bs: 2H, 3.86: bm: 2H, 6.37: s: 1H, 6.93: d: 1H, 6.98-7.11: 2s: 2H, 7.20-7.37: u.c.: 4H, 7.45: d: 2H, 7.58: d: 1H.

Compound 3
¹H NMR: DMSO-d6 (250 MHz): δ (ppm): 1.27-1.97: u.c.: 12H, 2.45: bs: 4H, 2.65: t: 2H, 2.92: t: 2H, 3.38: mt: 2H, 3.85: bd: 2H, 6.38: s: 1H, 6.96-7.13: 2s: 2H, 7.17-7.39: u.c.: 4H, 7.46: d: 2H, 7.58: d: 1H, 8.18: bs: 2H, 10.23: t: 1H.

Compound 4
¹H NMR: DMSO-d6 (250 MHz): δ (ppm): 1.31: quin: 2H, 1.79: mt: 2H, 2.52: mt: 2H, 2.62: t: 2H, 3.15: q: 2H, 3.23: bs: 2H, 4.10: bd: 2H, 4.44: t: 1H, 6.38: s: 1H, 7.07: s: 1H, 7.17-7.52: u.c.: 12H, 7.58: d: 1H.

Compound 5
¹H NMR: DMSO-d6 (400 MHz): δ (ppm): 1.63: quin: 2H, 1.74-2.06: u.c.: 6H, 2.53: mt: 2H, 2.70: t: 2H, 2.90: bs: 6H, 3.38: bt: 2H, 4.05: dt: 2H, 6.41: s: 1H, 6.85: bs: 2H, 7.18-7.58: u.c.: 12H.

Compound 6
¹H NMR: DMSO-d6 (400 MHz): δ (ppm): 1.41: quin: 2H, 1.81: mt: 2H, 2.53: u.c.: 2H, 2.62: t: 2H, 2.72: q: 2H, 2.74: s: 3H, 3.24: bs: 2H, 4.10: bs: 2H, 6.40: s: 1H, 6.91: t: 1H, 7.07: s: 1H, 7.18-7.60: u.c.: 13H.

Compound 7
¹H NMR: DMSO-d6 (400 MHz): δ (ppm): 1.30-1.99: u.c.: 10H, 2.53-2.71: u.c.: 4H, 2.74-3.01: mt: 4H, 3.10-3.26: mt: 4H, 3.38: t: 2H, 3.57: bd: 2H, 4.38: bd: 2H, 6.39: s: 1H, 7.05: bs: 1H, 7.17-7.38: mt: 4H, 7.45: d: 2H, 7.56: s: 1H.

Compound 8
¹H NMR: DMSO-d6 (250 MHz): δ (ppm): 1.60: mt: 6H, 1.64-1.97: u.c.: 4H, 2.46: bs: 4H, 3.35: t: 2H, 3.85: d: 2H, 4.31: d: 2H, 4.92: t: 1H, 6.42: s: 1H, 7.08: d: 2H, 7.21-7.51: mt: 6H, 7.60: d: 1H.

Compound 10
¹H NMR: DMSO-d6 (250 MHz): δ (ppm): 1.05-1.30: u.c.: 4H, 1.77: t: 2H, 2.37-2.54: u.c.: 2H, 2.54-2.67: u.c.: 2H, 3.06-3.32: u.c.: 4H, 3.90-4.18: u.c.: 2H, 4.22: t: 1H, 6.38: s: 1H, 7.12: s: 1H, 7.19-7.34: u.c.: 5H, 7.37-7.51: u.c.: 6H, 7.58: d: 1H.

Compound 13
¹H NMR: DMSO-d6 (250 MHz): δ (ppm): 1.02-1.28: u.c.: 4H, 1.78: t: 2H, 2.41-2.55: u.c.: 2H, 2.61: t: 2H, 3.14: q: 2H, 3.17-3.33: u.c.: 2H, 4.01-4.16: u.c.: 2H, 4.21: t: 1H, 6.38: s: 1H, 7.08: s: 1H, 7.16-7.54: u.c.: 12H, 7.58: d: 1H.

Compound 16
¹H NMR: DMSO-d6 (250 MHz): δ (ppm): 1.60: d: 2H, 1.82: t: 2H, 2.27-2.48: u.c.: 3H, 2.52-2.66: u.c.: 2H, 2.74: t: 2H, 3.20-3.33: u.c.: 2H, 3.34-3.56: u.c.: 2H, 3.76-3.95: u.c.: 2H, 4.76: t: 1H, 6.35: s: 1H, 7.11: s: 1H, 7.19-7.37: u.c.: 5H, 7.40-7.53: u.c.: 2H, 7.58: d: 1H.

Compound 18:
¹H NMR: DMSO-d6 (250 MHz): δ (ppm): 1.66-2.06: u.c.: 8H, 2.54-2.67: u.c.: 4H, 2.75: t: 2H, 3.21-3.35: u.c.: 2H, 3.37-3.50: u.c.: 2H, 3.73-3.95: u.c.: 2H, 4.76: t: 1H, 6.38: s: 1H, 7.16: s: 2H, 7.22-7.39: u.c.: 4H, 7.47: d: 2H, 7.58: d: 1H.

Compound 20:
¹H NMR: DMSO-d6 (250 MHz): δ (ppm): 1.66-1.82: u.c.: 2H, 1.84-1.99: u.c.: 2H, 2.13-2.31: u.c.: 2H, 2.74: t: 2H, 2.85: t: 2H, 3.08: t: 2H, 3.24-3.34: u.c.: 2H, 3.47-3.61: u.c.: 2H, 3.61-3.72: u.c.: 2H, 4.75: t: 1H, 6.38: s: 1H, 7.21: s: 1H, 7.26: dd: 4H, 7.33: dd: 1H, 7.46: d: 2H, 7.58: d: 1H.

Compound 24:
¹H NMR: DMSO-d6 (250 MHz): δ (ppm): 1.20-1.38: u.c.: 4H, 1.63-1.98: u.c.: 4H, 2.37-2.48: u.c.: 4H, 2.73: t: 2H, 3.20-3.33: u.c.: 2H, 3.32-3.51: u.c.: 2H, 3.73-3.93: u.c.: 2H, 4.76: t: 1H, 6.38: s: 1H, 7.07: d: 2H, 7.21-7.37: u.c.: 4H, 7.47: d: 2H, 7.58: d: 1H.

Compound 27:
¹H NMR: DMSO-d6 (250 MHz): δ (ppm): 0.85: s: 6H, 1.25-1.34: u.c.: 4H, 1.35-1.50: u.c.: 2H, 1.62-2.04: u.c.: 4H, 2.36-2.48: u.c.: 4H, 2.56-2.67: u.c.: 2H, 2.68-2.78: u.c.: 2H, 2.77: s: 3H, 3.31-3.50: u.c.: 2H, 3.72-3.95: u.c.: 2H, 6.38: s: 1H, 6.94: t: 1H, 7.02-7.15: u.c.: 2H, 7.25: d: 2H, 7.29-7.34: u.c.: 2H, 7.46: d: 2H, 7.58: d: 1H.

Compound 28:
¹H NMR: DMSO-d6 (250 MHz): δ (ppm): 0.85: s: 6H, 1.18-1.52: u.c.: 6H, 1.65-2.09: u.c.: 4H, 2.37-2.47: u.c.: 4H, 2.56-2.67: u.c.: 2H, 3.15: q: 2H, 3.33-3.46: u.c.: 2H, 3.77-3.93: u.c.: 2H, 4.48: t: 1H, 6.36: s: 1H, 7.02-7.16: u.c.: 2H, 7.19-7.34: u.c.: 4H, 7.46: d: 2H, 7.58: d: 1H.

Compound 29:
¹H NMR: DMSO-d6 (250 MHz): δ (ppm): 1.29-1.50: u.c.: 2H, 1.65-1.90: u.c.: 2H, 2.37-2.51: u.c.: 2H, 2.66-2.81: u.c.: 5H, 3.05-3.28: u.c.: 2H, 3.86-4.30: u.c.: 2H, 6.40: s: 1H, 6.92: t: 1H, 7.10-7.20: u.c.: 1H, 7.21-7.37: u.c.: 6H, 7.37-7.55: u.c.: 7H, 7.59: d: 1H.

Compound 30:
¹H NMR: DMSO-d6 (250 MHz): δ (ppm): 1.23-1.40: u.c.: 2H, 1.68-1.87: u.c.: 2H, 2.37-2.50: u.c.: 2H, 2.55-2.68: u.c.: 2H, 3.14: q: 2H, 3.17-3.31: u.c.: 2H, 3.93-4.25: u.c.: 2H, 4.46: t: 1H, 6.39: s: 1H, 7.16: s: 1H, 7.20-7.34: u.c.: 5H, 7.42: s, 6H, 7.59: d: 1H.

Compound 31:
¹H NMR: DMSO-d6 (250 MHz): δ (ppm): 1.25-1.43: u.c.: 2H, 1.65-2.08: u.c.: 8H, 2.53-2.72: u.c.: 6H, 3.15: q: 2H, 3.36-3.57: u.c.: 2H, 3.70-3.91: u.c.: 2H, 4.49: t: 1H, 6.37: s: 1H, 7.17: s: 2H, 7.24: d: 2H, 7.30: s: 1H, 7.32: d: 1H, 7.46: d: 2H, 7.58: d: 1H.

Compound 32:
¹H NMR: DMSO-d6 (400 MHz): δ (ppm): 1.33-1.49: u.c.: 2H, 1.69-1.84: u.c.: 2H, 1.86-2.00: u.c.: 2H, 2.14-2.31: u.c.: 2H, 2.58-2.66: u.c.: 2H, 2.73: q: 2H, 2.78: s: 3H, 2.85: t: 2H, 3.08: t: 2H, 3.48-3.60: u.c.: 2H, 3.61-3.76: u.c.: 2H, 6.39: s: 1H, 6.93: t: 1H, 7.20: s: 1H, 7.22-7.36: u.c.: 5H, 7.46: d: 2H, 7.58: d: 1H.

Compound 33:
¹H NMR: DMSO-d6 (250 MHz): δ (ppm): 1.31-1.55: u.c.: 2H, 1.66-2.09: u.c.: 8H, 2.53-2.67: u.c.: 6H, 2.73: q: 2H, 2.77: s: 3H, 3.38-3.63: u.c.: 2H; 3.72-3.94: u.c.: 2H, 6.38: s: 1H, 6.94: t: 1H, 7.17: s: 2H, 7.25: d: 2H, 7.29-7.35: u.c.: 2H, 7.47: d: 2H, 7.59: d: 1H.

Compound 34:
¹H NMR: DMSO-d6 (250 MHz): δ (ppm): 1.22-1.40: u.c.: 2H, 1.66-1.91: u.c.: 2H, 2.42-2.56: u.c.: 2H, 2.56-2.68: u.c.: 2H, 3.14: q: 2H, 3.11-3.32: u.c.: 2H, 3.96-4.25: u.c.: 2H, 4.48: t: 1H, 6.35: s: 1H, 7.05-7.20: u.c.: 2H, 7.20-7.30: u.c.: 4H, 7.30-7.57: u.c.: 8H.

Compound 35:
¹H NMR: DMSO-d6 (400 MHz): δ (ppm): 0.00-0.16: u.c.: 2H, 0.35-0.50: u.c.: 2H, 0.80-0.96: u.c.: 1H, 1.27-1.40: u.c.: 2H, 1.52-1.65: u.c.: 2H; 1.73-1.86: u.c.: 2H, 2.09: br. s.: 1H, 2.20: d: 2H, 2.63: t: 2H, 3.17: q: 2H, 3.39-3.64: u.c.: 2H, 3.70-3.93: u.c.: 2H, 4.49: t: 1H, 6.29: s: 1H, 6.99: s: 1H, 7.08-7.17: u.c.: 1H, 7.23: d; 2H, 7.27-7.37: u.c.: 2H, 7.39: dd: 1H, 7.44: d 2H.

Compound 36:
¹H NMR: DMSO-d6 (250 MHz): δ (ppm) 1.24-1.40: u.c.: 2H, 1.40-1.62: u.c.: 2H, 1.64-1.84: u.c.: 2H, 2.31-2.46: u.c.: 1H, 2.61: t: 2H, 2.80-3.04: u.c.: 2H, 3.04-3.24: u.c.: 4H, 3.37: q: 2H, 4.15-4.39: u.c.: 2H, 4.47: t: 1H, 4.63: t: 1H, 6.29: s: 1H, 7.06-7.19: u.c.: 1H, 7.24: d: 2H, 7.29-7.50: u.c.: 4H, 7.81: s: 1H Compound 37:
¹H NMR: DMSO-d6 (250 MHz): δ (ppm) 1.06-1.40: u.c.: 4H, 1.59-2.05: u.c.: 6H, 2.06-2.36: u.c.: 2H, 2.53-2.67: u.c.:

2H, 2.74-2.95: u.c.: 2H, 3.01-3.20: u.c.: 2H, 3.46-3.77: u.c.: 4H, 6.37: s: 1H, 6.58: s: 1H, 7.12: s: 1H, 7.18-7.40: u.c.: 6H, 7.46: d: 2H, 7.57: d: 1H.

Compound 38:
$^1$H NMR: DMSO-d6 (250 MHz): δ (ppm) 1.63-2.00: u.c.: 4H, 2.02-2.39: u.c.: 4H, 2.66-2.80: u.c.: 2H, 2.80-2.94: u.c.: 2H, 3.10: t, 2H, 3.46-3.78: u.c.: 4 H, 6.38: s: 1H, 6.65: s: 1H, 7.14: s: 1H, 7.18-7.38: u.c.: 7H, 7.46: d: 2H, 7.58: d: 1H.

Compound 39:
$^1$H NMR: DMSO-d6 (250 MHz): δ (ppm) 1.70-1.90: u.c.: 2H, 2.01-2.16: u.c.: 2H, 2.45-2.58: u.c.: 2H, 2.67-2.81: u.c.: 2H, 3.34: s: 2H, 3.90-4.21: u.c.: 2H, 6.37: s: 1H, 6.63: s: 1H, 7.03-7.17: u.c.: 2H, 7.18-7.52: u.c.: 12H, 7.57: d: 1H.

Compound 40:
$^1$H NMR: DMSO-d6 (250 MHz): δ (ppm) 1.02-1.42: u.c.: 4H, 1.65-1.96: u.c.: 4H, 2.38-2.64: u.c.: 4H, 3.08-3.38: u.c.: 2H, 3.95-4.20: u.c.: 2H, 6.38: s: 1H, 6.56: s: 1H, 7.02-7.16: u.c.: 2H, 7.17-7.52: u.c.: 12H, 7.58: d: 1H.

Compound 41:
$^1$H NMR: DMSO-d6 (250 MHz): δ (ppm) 1.24-1.40: u.c.: 2H, 1.63-1.82: u.c.: 2H, 1.82-1.96: u.c.: 2H, 2.09-2.33: u.c.: 2H, 2.55-2.68: u.c.: 2H, 2.79-2.90: u.c.: 2H, 3.05: d: 1H, 3.11-3.23: u.c.: 3H, 3.45-3.75: u.c.: 4H, 4.47: t: 1H, 6.33: s: 1H, 7.08-7.29: u.c.: 5H, 7.30-7.50: u.c.: 4H.

Compound 42:
$^1$H NMR: DMSO-d6 (250 MHz): δ (ppm) 1.31-1.54: u.c.: 2H, 1.69-1.93: u.c.: 4H, 2.42-2.69: u.c.: 4H, 3.07-3.28: u.c.: 2H, 4.01-4.32: u.c.: 2H, 6.35: s: 1H, 6.60: s: 1H, 7.04-7.33: u.c.: 10H, 7.35-7.54: u.c.: 5H.

Compound 43:
$^1$H NMR: DMSO-d6 (250 MHz): δ (ppm) −0.01-0.12: u.c.: 2H, 0.34-0.46: u.c.: 2H, 0.75-0.96: u.c.: 1H, 1.30-1.49: u.c.: 2H, 1.49-1.67: u.c.: 2H, 1.69-1.88: u.c.: 2H, 2.07: br. s.: 1H, 2.13-2.29: u.c.: 2H, 2.56-2.67: u.c.: 2H, 2.72: q: 2H, 2.78: s: 3H, 3.40-3.64: u.c.: 2H, 3.66-3.91: u.c.: 2H, 6.36: s: 1H; 6.94: t: 1H, 6.99-7.05: u.c.: 1H, 7.18-7.34: u.c.: 5H, 7.45: s: 2H, 7.58: d: 1H.

Compound 44:
$^1$H NMR: DMSO-d6 (250 MHz): δ (ppm) 0.02-0.14: u.c.: 2H, 0.33-0.45: u.c.: 2H, 0.74-0.94: u.c.: 1H, 1.22-1.38: u.c.: 2H, 1.50-1.66: u.c.: 2H, 1.69-1.86: u.c.: 2H, 2.19: d: 2H, 2.62: t: 2H, 3.16: q: 2H, 3.41-3.66: u.c.: 2H, 3.68-3.92: u.c.: 2H, 4.45: t: 1H, 6.34: s: 1H, 7.02: s: 1H, 7.17-7.36: u.c.: 5H, 7.46: d: 2H, 7.58: d: 1H.

Compound 45:
$^1$H NMR: DMSO-d6 (250 MHz): δ (ppm) 0.94-1.15: u.c.: 2H, 1.17-1.32: u.c.: 2H, 1.31-1.62: u.c.: 5H, 1.61-1.81: u.c.: 2H, 2.62: t: 2H, 2.73: q: 2H, 2.78: s: 3H, 2.80-3.03: u.c.: 2H, 3.38: q: 2H, 4.11-4.35: u.c.: 2H, 4.35: t: 1H, 6.33: s: 1H, 6.94: t: 1H, 7.19-7.34: u.c.: 4H, 7.46: d: 2H, 7.58: d: 1H.

Compound 46:
$^1$H NMR: DMSO-d6 (250 MHz): δ (ppm) 0.92-1.15: u.c.: 2H, 1.15-1.60: u.c.: 7H, 1.70: d: 2H, 2.62: t: 2H, 2.66-3.06: u.c.: 2H, 3.17: q: 2H, 3.38: q: 2H, 4.16-4.33: u.c.: 2H, 4.35: t: 1H, 4.48: t: 1H, 6.31: s: 1H, 7.24: d: 2H, 7.28-7.37: u.c.: 2H, 7.46: d: 2H, 7.58: d: 1H.

Compound 47:
$^1$H NMR: DMSO-d6 (400 MHz): δ (ppm) 1.33-1.49: u.c.: 2H, 1.73-1.89: u.c.: 2H, 2.46-2.54: u.c.: 2H, 2.62: t: 2H, 2.72: q: 2H, 2.75: s: 3H, 3.02-3.27: u.c.: 2H, 3.92-4.31: u.c.: 2H, 6.40: s: 1H, 6.90: t: 1H, 7.10: s: 1H, 7.17: t: 2H, 7.21-7.38: u.c.: 5H, 7.39-7.50: u.c.: 4H, 7.58: s: 1H.

Compound 48:
$^1$H NMR: DMSO-d6 (250 MHz): δ (ppm) 1.24-1.42: u.c.: 2H, 1.66-1.86: u.c.: 2H, 2.43-2.56: u.c.: 2H, 2.62: t: 2H, 3.15: q: 2H, 3.14-3.26: u.c.: 2H, 3.99-4.21: u.c.: 2H, 4.43: t: 1H, 6.38: s: 1H, 7.10: s: 1H, 7.13-7.37: u.c.: 7H, 7.38-7.52: u.c.: 4H, 7.58: d: 1H.

Compound 49:
$^1$H NMR: DMSO-d6 (250 MHz): δ (ppm) 1.05-1.36: u.c.: 4H, 1.66-1.90: u.c.: 4H, 2.42-2.51: u.c.: 2H, 2.54-2.69: u.c.: 2H, 3.04-3.28: u.c.: 2H, 3.93-4.23: u.c.: 2H, 6.38: s: 1H, 6.57: s: 1H, 7.03-7.36: u.c.: 9H, 7.40-7.54: u.c.: 4H, 7.57: d: 1H.

Compound 50:
$^1$H NMR: DMSO-d6 (250 MHz): δ (ppm) 1.21-1.44: u.c.: 2H, 1.66-1.88: u.c.: 2H, 2.44-2.54: u.c.: 2H, 2.62: t: 2H, 3.15: q: 2H, 3.15-3.28: u.c.: 2H, 3.97-4.19: u.c.: 2H, 4.44: t: 1H, 6.34: s: 1H, 7.03-7.28: u.c.: 7H, 7.30-7.51: u.c.: 6H.

The compounds of formula (I) possess a very good affinity in vitro ($IC_{50} \leq 5.10^{-7}$M) for the $CB_1$ cannabinoid receptors under the experimental conditions described by M. Rinaldi-Carmona et al. (FEBS Letters, 1994, 350, 240-244).

The antagonist nature of the compounds of formula (I) was demonstrated in vitro by the results obtained in the adenylate cyclase inhibition models as described in M. Bouaboula et al., J. Biol. Chem., 1995, 270, 13973-13980, M. Rinaldi-Carmona et al., J. Pharmacol. Exp. Ther., 1996, 278, 871-878 and M. Bouaboula et al., J. Biol. Chem., 1997, 272, 22330-22339.

The weak penetration of the compounds of formula (I) at the level of the blood-brain barrier (BBB) was evaluated in vivo by:

Measurement (1): the quantification of the compounds of formula (I) (unchanged) in samples of mouse brain after intravenous or oral administration, with the aid of an analytical technique (LC-MS/MS).

The ratio $\frac{\text{quantity present in the brain}}{\text{quantity present in the plasma}}$ less than 0.2 indicates a weak penetration of the compound at the level of the brain.

Measurement (2): the measurement of the interaction of the compounds of formula (I) with the $CB_1$ receptors present in the brain in mice with the aid of an ex vivo test of binding of [3H]-CP55940 ($CB_1$ agonist) after administration by the intravenous route (10 mg/kg) as described in M. Rinaldi-Carmona et al., FEBS Letters, 1994, 350, 240-244 and M. Rinaldi-Carmona et al., Life Sciences, 1995, 56, 1941-1947, M. Rinaldi-Carmona et al., J. Pharmacol. Exp. Ther., 2004, 310, 905-914.

A percentage inhibition of the binding of [3H]-CP55940 at the level of the brain of less than 50% at 10 mg/kg indicates a weak penetration at the level of the brain. Preferably, this percentage is less than 40% and more preferably less than 30%.

Measurement (3): the measurement of the blocking, by the compounds of formula (I), of the hypothermic effect induced by an agonist of the $CB_1$ receptors (CP55940), after administration by the intravenous route, as described in Rinaldi-Carmona M. et al., JPET 2004, 310, 905-914.

A percentage reversion of the effect of CP55940 of less than or equal to 60% at 10 mg/kg indicates a weak penetration at the level of the brain. Preferably, this percentage is less than 40% and more preferably less than 30%.

The interaction of the compounds of formula (I) according to the invention with the $CB_1$ receptors present at the periphery was demonstrated in mice by measuring the blocking of the inhibitory effect induced by an agonist of the $CB_1$ receptors (CP55940) on the gastrointestinal transit, after oral administration, as described in M. Rinaldi-Carmona et al., J. Pharmacol. Exp. Ther., 2004, 310, 905-914. A percentage reversion of the effect of CP55940 greater than 50% at 10 mg/kg indicates a significant antagonist power at the level of the CB$_1$ receptors present at the periphery. Preferably, the percentage reversion is between 70% and 100%.

By way of examples, the following measurements were performed for compound Nos. 13, 14, 17 and 30 of Table 1.

| | Ratio: Quantity present in the brain Quantity present in the plasma [iv route at 3 mg/kg, according to measurement (1)] | % inhibition of the binding of [3H]-CP55940 in the brain, by the iv route at 10 mg/kg [CB$_1$ receptors present in the brain according to measurement (2)]. | % reversion of the hypothermic effect of CP55940, by the iv route at 10 mg/kg [CB$_1$ receptors present in the brain, according to measurement (3)]. | % reversion of the effect of CP55940 on the GIT by the po route at 10 mg/kg [CB$_1$ receptors present at the periphery]. |
|---|---|---|---|---|
| Control: rimonabant | 1.8 | 100% | 100% [effective dose 50 (ED$_{50}$) = 0.3 mg/kg] | 100% |
| Compound No. 13 | | 5% | 58% | 100% |
| Compound No. 14 | | 27% | 60% | 85% |
| Compound No. 17 | | 23% | 60% | 97% |
| Compound No. 30 | 0.06 | 21% | 32% | 74% |

The compounds of formula (I) are compatible with their use as a medicament.

Thus, according to another of its aspects, the subject of the invention is medicaments for human or veterinary medicine which comprise a compound of formula (I), or an addition salt thereof with a pharmaceutically acceptable acid.

Thus, the compounds according to the invention may be used in humans or in animals (in particular in mammals including, without limitation, dogs, cats, horses, bovines, sheep) in the treatment or prevention of diseases involving the CB$_1$ cannabinoid receptors.

For example and without limitation, the compounds of formula (I) are useful as psychotropic medicaments, in particular for the treatment of psychiatric disorders including anxiety, depression, mood disorders, insomnia, delirium disorders, obsessive disorders, psychoses in general, schizophrenia, attention deficit hyperactivity disorders (ADHD) in hyperkinetic children and for the treatment of disorders linked to the use of psychotropic substances, in particular in the case of substance abuse and/or of dependence on a substance, including alcohol dependence and nicotine dependence.

The compounds of formula (I) according to the invention may be used as medicaments for the treatment of migraine, stress, diseases of psychosomatic origin, panic attacks, epilepsy, motion disorders, in particular dyskinesia or Parkinson's disease, tremors and dystonia.

The compounds of formula (I) according to the invention may also be used as medicaments in the treatment of memory disorders, cognitive disorders, in particular in the treatment of senile dementia, Alzheimer's disease, and in the treatment of attention or vigilance disorders.

Furthermore, the compounds of formula (I) may be useful as neuroprotectants, in the treatment of ischaemia, cranial traumas and the treatment of acute or chronic neurodegenerative diseases: including chorea, Huntington's chorea, Tourrette's syndrome.

The compounds of formula (I) according to the invention may be used as medicaments in the treatment of pain: neuropathic pain, acute peripheral pain, chronic pain of inflammatory origin, pain induced by an anticancer treatment.

The compounds of formula (I) according to the invention may be used as medicaments in human or veterinary medicine in the prevention and treatment of appetite disorders, craving disorders (for sugars, carbohydrates, drugs, alcohol or any appetizing substance) and/or alimentary canal disorders, in particular for the treatment of obesity or bulimia and for the treatment of type II diabetes or non-insulin-dependent diabetes and for the treatment of dyslipidemia, and of metabolic syndrome. Thus, the compounds of formula (I) according to the invention are useful in the treatment of obesity and of the risks associated with obesity, in particular the cardiovascular risks.

Furthermore, the compounds of formula (I) according to the invention may be used as medicaments in the treatment and prevention of gastrointestinal disorders, diarrhoeal disorders, ulcers, emesis, bladder and urinary disorders, liver diseases of alcohol or non-alcohol origin such as chronic cirrhosis, fibrosis, hepatic steatosis, steatohepatitis; and disorders of endocrine origin, cardiovascular disorders, hypotension, atherosclerosis, haemorrhagic shock, septic shock, asthma, chronic bronchitis, chronic obstructive pulmonary disease, Raynaud's syndrome, glaucoma, fertility disorders, premature labour, abortion, inflammatory phenomena, immune system diseases, in particular autoimmune and neuroinflammatory diseases such as rheumatoid arthritis, reactive arthritis, diseases causing demyelinization, multiple sclerosis, infectious and viral diseases such as encephalitis, stroke and as medicaments for anticancer chemotherapy, for the treatment of Guillain-Barré syndrome and for the treatment of bone diseases and of osteoporosis. Furthermore, the compounds of formula (I) according to the invention may be used for their protective effects against drug-induced cardiotoxicity.

According to the present invention, the compounds of formula (I) are most particularly useful for the preparation of medicaments useful for the prevention and treatment of psychiatric disorders, in particular schizophrenia, attention and vigilance disorders, attention deficit and hyperactivity disorders (ADHD) in hyperkinetic children; for the prevention and treatment of memory deficiencies and cognitive disorders;

dependence and withdrawal from a substance, in particular alcohol dependence, nicotine dependence, withdrawal from alcohol and smoking cessation; acute or chronic neurodegenerative diseases.

More particularly, the compounds of formula (I) according to the present invention are useful in the preparation of medicaments useful in the treatment and prevention of appetite disorders, craving disorders, metabolism disorders, obesity, type II diabetes, metabolic syndrome, dyslipidemia, gastrointestinal disorders, inflammatory phenomena, diseases of the immune system, psychotic disorders, alcohol dependence, nicotine dependence.

According to one of its aspects, the present invention relates to the use of a compound of formula (I) and of its pharmaceutically acceptable salts for the treatment of disorders and diseases indicated above.

According to another of its aspects, the present invention relates to pharmaceutical compositions comprising, as active ingredient, a compound according to the invention. These pharmaceutical compositions contain an effective dose of at least one compound according to the invention, or a pharmaceutically acceptable salt of the said compound, and at least one pharmaceutically acceptable excipient.

The said excipients are chosen according to the pharmaceutical dosage form and the mode of administration desired, from the customary excipients which are known to persons skilled in the art.

Pharmaceutical compositions according to the present invention may contain, in addition to a compound of formula (I), one (or more) other active ingredient(s) useful in the treatment of the disorders and diseases indicated above.

Thus, the subject of the present invention is also pharmaceutical compositions containing a compound of formula (I) according to the present invention combined with one (or more) active ingredient(s) chosen from one of the following therapeutic classes:

another antagonist or allosteric modulators of the $CB_1$ cannabinoid receptors;
a modulator of the $CB_2$ cannabinoid receptors;
an antagonist of the $AT_1$ receptors for angiotensin II;
a converting enzyme inhibitor;
a calcium antagonist;
a diuretic;
a beta-blocker;
an antihyperlipemic or an antihypercholesterolemic;
an antidiabetic;
another anti-obesity agent or agent acting on metabolism disorders;
a nicotine agonist, a partial nicotine agonist;
an antidepressant, an antipsychotic, an anxiolytic;
an anticancer agent or an antiproliferative agent;
an opioid antagonist;
as well as:
a memory enhancer;
an agent useful in the treatment of alcoholism or of withdrawal symptoms;
an agent useful for treating osteoporosis;
a steroidal or non-steroidal anti-inflammatory agent;
an antiinfective;
an analgesic;
an antiasthmatic.

The expression antagonist of the $AT_1$ receptors for angiotensin II is understood to mean a compound such as candesartan cilexitil, eprosartan, irbesartan, losartan potassium, olmesartan medoxomil, telmisartan, valsartan, it being possible for each of these compounds themselves to be combined with a diuretic such as hydrochlorothiazide.

The expression converting enzyme inhibitor is understood to mean a compound such as alacepril, benazepril, captopril, cilazapril, enalapril, enalaprilat, fosinopril, imidapril, lisinopril, moexipril, perindopril, quinapril, ramipril, spirapril, temocapril, trandolapril, zofenopril, it being possible for each of these compounds themselves to be combined with a diuretic such as hydrochlorothiazide or indapamide or with a calcium antagonist such as amlodipine, diltiazem, felodipine or verapamil.

The expression calcium antagonist is understood to mean a compound such as amlodipine, aranidipine, benidipine, bepridil, cilnidipine, diltiazem, efonidipine hydrochloride ethanol, fasudil, felodipine, isradipine, lacidipine, lercanidipine hydrochloride, manidipine, mibefradil hydrochloride, nicardipine, nifedipine, nilvadipine, nimodipine, nisoldipine, nitrendipine, terodiline, verapamil.

The expression beta-blocker is understood to mean a compound such as acebutolol, alprenolol, amosulalol, arotinolol, atenolol, befunolol, betaxolol, bevantolol, bisoprolol, bopindolol, bucumolol, bufetolol, bunitrolol, butofilolol, carazolol, carteolol, carvedilol, cloranolol, epanolol, esmolol, indenolol, labetalol, landiolol, levobunolol, levomoprolol, mepindolol, metipranolol, metoprolol, nadolol, nebivolol, nifenalol, nipradilol, oxprenolol, penbutolol, pindolol, propranolol, salmeterol, sotalol, talinolol, tertatolol, tilisolol, timolol, xamoterol, xibenolol.

The expression antihyperlipemic or antihypercholesterolemic is understood to mean a compound chosen from fibrates such as alufibrate, beclobrate, bezafibrate, ciprofibrate, clinofibrate, clofibrate, etofibrate, fenofibrate; statins (HMG-CoA reductase inhibitors), such as atorvastatin, fluvastatin sodium, lovastatin, pravastatin, rosuvastatin, simvastatin, or a compound such as acipimox, aluminium nicotinate, azacosterol, cholestyramine, dextrothyroxine, meglutol, niceritrol, nicoclonate, nicotinic acid, beta-sitosterol, tiadenol.

The expression antidiabetic is understood to mean a compound belonging to one of the following classes: sulphonylureas, biguanidines, alpha glucosidase inhibitors, thiazolidinediones, metiglinides, such as acarbose, acetohexamide, carbutamide, chlorpropamide, glibenclamide, glibornuride, gliclazide, glimepiride, glipizide, gliquidone, glisoxepide, glybuzole, glymidine, metahexamide, metformin, miglitol, nateglinide, pioglitazone, repaglinide, rosiglitazone, tolazamide, tolbutamide, troglitazone, voglibose, as well as insulin and insulin analogues.

The expression another anti-obesity agent or agent acting on metabolism disorders is understood to mean a compound such as amfepramone, benfluorex, benzphetamine, indanorex, mazindole, mefenorex, methamphetamine, D-norpseudoephedrine, sibutramine, a topiramate, a lipase inhibitor (orlistat cetilistat), a PPAR agonist (Peroxisome Proliferator Activated Receptor Agonist), a dopamine agonist, a leptin receptor agonist, a serotonin reuptake inhibitor, a beta-3 agonist, a CCK-A agonist, an NPY inhibitor, an agonist of the MC 4 (melanocortin 4) receptors, an antagonist of the MCH (Melanin Concentrating Hormone) receptors, an orexin antagonist, a phosphodiesterase inhibitor, an 11β-HSD (11-β-hydroxysteroid deshydrogenase) inhibitor, a DPP-IV (dipeptidyl peptidase IV) inhibitor, an antagonist (or inverse agonist) of histamine H3, a CNTF (Ciliary Neurotrophic Factor) derivative, an agonist of the GHS (Growth Hormone Secretagogue) receptors, a ghrelin modulator, a diacyglycerol acyltransferase (DGAT) inhibitor, a phosphodiesterase (PDE) inhibitor, a thyroid hormone agonist, an antagonist of the glucocorticoid receptors, a stearoyl-CoA-desaturase (SCD) inhibitor, a modulator of phosphate, glucose, fatty acid and dicarboxylate transporters, a 5HT$_2$ antagonist, a 5HT$_6$ antagonist, a bombesine agonist.

The expression opioid antagonist is understood to mean a compound such as naltrexone, naloxone ou nalmefene.

The expression agent useful in the treatment of alcoholism and withdrawal symptoms is understood to mean acamprosate, benzodiazepines, beta-blockers, clonidine, carbamazepine.

The expression agent useful for treating osteoporosis is understood to mean for example biphosphonates such as etidronate, clodronate, tiludronate, risedronate.

According to the present invention, it is also possible to combine other compounds having antihyperlipemic, antihypercholesterolemic, antidiabetic or anti-obesity properties. More particularly, it is possible to combine compounds belonging to one of the following classes:
PTP 1 B (Protein Tyrosine Phosphase-1B) inhibitors, agonists of the VPAC 2 receptors, GLK modulators, retinoid modulators, glycogen phosphorylase (HGLPa) inhibitors, glucagon antagonists, glucose-6-phosphate inhibitors, pyruvate dehydrogenase kinase (PDK) activators, modulators of RXR, FXR, LXR, inhibitors of SGLT (Sodium Dependant Glucose Transporter), CETP (Cholesteryl ester Transfer Protein) inhibitors, squalene synthetase inhibitors, squalene epoxidase inhibitors, triglyceride synthesis inhibitors, inducers of LDL (Low Density Lipoprotein) receptors, IBAT inhibitors, FBPase (fructose-1,6-biphosphatase) inhibitors, CART (Cocaine-Amphetamine-Regulated Transcript) modulators, antagonists of the orexin receptors.

According to another aspect of the invention, the compound of formula (I), one of its pharmaceutically acceptable salts and the other associated active ingredient may be administered simultaneously, separately or spread out over time.

The expression "simultaneous use" is understood to mean the administration of the compounds of the composition according to the invention contained in the same pharmaceutical dosage form.

The expression "separate use" is understood to mean the administration, at the same time, of two compounds of the composition according to the invention, each contained in a separate pharmaceutical dosage form.

The expression "use spread out over time" is understood to mean the successive administration of the first compound of the composition of the invention, contained in a pharmaceutical dosage form, followed by the second compound of the composition according to the invention, contained in a separate pharmaceutical dosage form. In this case, the time lapse between the administration of the first compound of the composition according to the invention and the administration of the second compound of the same composition according to the invention generally does not exceed 24 hours.

In the pharmaceutical compositions of the present invention for oral, sublingual, subcutaneous, intramuscular, intravenous, topical, local, intratracheal, intranasal, transdermal or rectal administration, the active ingredient of formula (I) above, or its salt, may be administered in a unit form for administration, mixed with conventional pharmaceutical excipients, to animals and to human beings for the prophylaxis or treatment of the above disorders or diseases.

The appropriate unit forms for administration comprise the oral forms such as tablets, soft or hard gelatin capsules, powders, granules and oral solutions or suspensions, forms for sublingual, buccal, intratracheal, intraocular or intranasal administration or for administration by inhalation, forms for topical, transdermal, subcutaneous, intramuscular or intravenous administration, forms for rectal administration and implants. For topical application it is possible to use the compounds according to the invention in creams, gels, ointments or lotions.

By way of example, a unit form for administration of a compound according to the invention in tablet form may comprise the following components:

| | |
|---|---|
| Compound according to the invention | 50.0 mg |
| Mannitol | 223.75 mg |
| Croscarmellose sodium | 6.0 mg |
| Maize starch | 15.0 mg |
| Hydroxypropylmethylcellulose | 2.25 mg |
| Magnesium stearate | 3.0 mg |

By the oral route, the dose of active ingredient administered per day may be up to 0.01 to 100 mg/kg, in single or divided doses, preferably 0.02 to 50 mg/kg.

There may be specific cases where higher or lower dosages are appropriate; such dosages do not depart from the scope of the invention. According to the customary practice, the dosage appropriate for each patient is determined by the doctor according to the mode of administration, the weight and the response of the said patient.

The present invention, according to another of its aspects, also relates to a method for treating the pathologies indicated above, which comprises the administration, to a patient, of an effective dose of a compound according to the invention, or of one of its pharmaceutically acceptable salts.

The invention claimed is:
1. A Compound of formula (I):

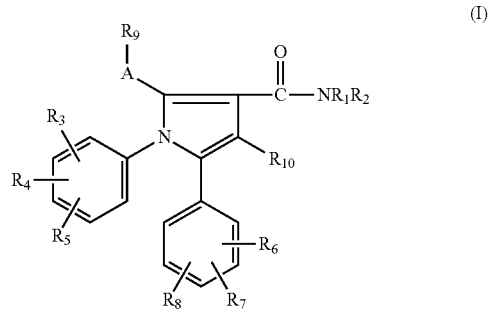

in which:
A represents a (C$_1$-C$_6$)alkylene group which is unsubstituted or substituted one or more times with a (C$_1$-C$_3$)alkyl group or a fluorine atom;
R$_1$ and R$_2$ together with the nitrogen atom to which they are attached constitute:
either a piperazin-1-yl or 1,4-diazepan-1-yl radical, the said radicals being unsubstituted or substituted with a phenyl, benzodioxolyl, benzodioxolylmethyl, tetrahydrofuranylcarbonyl, —COR$_{11}$, and/or —CH$_2$COR$_{11}$ group; the phenyl group being itself unsubstituted or substituted once or several times with a substituent each independently chosen from a halogen atom, a (C$_1$-C$_4$)alkyl, trifluoromethyl, hydroxyl, (C$_1$-C$_4$)alkoxy or cyano group;
or a homopiperidin-1-yl, piperidin-1-yl, pyrrolidin-1-yl or azetidin-1-yl radical, the said radicals being unsubstituted or substituted once or twice with a substituent each independently chosen from:

a fluorine atom, a cyano, —$COR_{11}$, —$CONR_{12}R_{13}$, —$NR_{12}R_{13}$, —$NHCOR_{14}$, —$CH_2COR_{11}$, —$SO_2R_{14}$ group; and/or —$SO_2 NR_{12}R_{13}$;

or a ($C_1$-$C_4$)alkyl group which is unsubstituted or substituted with one or more substituents each independently chosen from a halogen atom and/or a hydroxyl, or a phenyl or pyridinyl group; the said groups being unsubstituted or substituted once or several times with a substituent each independently chosen from a halogen atom, a ($C_1$-$C_4$)alkyl, trifluoromethyl, hydroxyl, ($C_1$-$C_4$)alkoxy or cyano group;

or a benzyl group which is unsubstituted or substituted once or several times with a substituent each independently chosen from a halogen atom, a ($C_1$-$C_4$)alkyl, trifluoromethyl, hydroxyl, ($C_1$-$C_4$) alkoxy or cyano group;

or a piperidin-1-yl, pyrrolidin-1-yl or azetidin-1-yl group, the said groups being unsubstituted or substituted once or several times with a substituent each independently chosen from a fluorine atom, a ($C_1$-$C_4$)alkyl, ($C_1$-$C_4$)alkoxy, hydroxyl, trifluoromethyl or —$OCF_3$ group;

or an aminophenyl or aminobenzyl group, the said groups being unsubstituted or substituted once or several times with a substituent each independently chosen from a halogen atom, a methyl, trifluoromethyl, hydroxyl, ($C_1$-$C_4$)alkoxy or cyano group;

or an amino($C_3$-$C_7$)cycloalkyl group which is unsubstituted or substituted once or several times with a substituent each independently chosen from a halogen atom, a hydroxyl, ($C_1$-$C_4$)alkyl, ($C_1$-$C_4$)alkoxy or cyano group, the said ($C_1$-$C_4$)alkyl group being unsubstituted or substituted once or several times with a fluorine atom;

$R_3$, $R_4$, $R_5$, $R_6$, $R_7$, $R_8$ each independently represent a hydrogen atom, a halogen atom, a —CN, —$S(O)_nR_{14}$ or —$OS(O)_nR_{14}$ group, or a ($C_1$-$C_6$)alkyl group which is unsubstituted or substituted once or several times with a substituent each independently chosen from a fluorine atom, an —OH, —$OR_{14}$, —$S(O)_nR_{14}$, —$OSO_2R_{14}$ or —$NHSO_2R_{14}$ group, or a ($C_1$-$C_6$) alkoxy group, which is unsubstituted or substituted with one or more substituents each independently chosen from a fluorine atom, an —OH, —$OR_{14}$, —$S(O)_nR_{14}$, —$OSO_2R_{14}$ or —$NHSO_2R_{14}$ group;

$R_9$ represents an —$OR_{12}$, —CN, —$CO_2H$, $NR_{12}R_{13}$, —$CONR_{12}R_{13}$, —$NR_{12}R_{13}$, —$NR_{15}COR_{12}$, —$CONHNH_2$, —CONHOH, —$CONHSO_2R_{14}$, —$S(O)_nR_{14}$, —$SO_2NR_{12}R_{13}$, —$NR_{18}SO_2R_{14}$ or —$NR_{15}SO_2NR_{12}R_{13}$ group;

$R_{10}$ represents a hydrogen or a ($C_1$-$C_4$)alkyl group;

$R_{11}$ represents:

a ($C_1$-$C_4$)alkyl, phenyl, benzyl, ($C_1$-$C_4$)alkoxy, or ($C_1$-$C_3$)alkylene-O—($C_1$-$C_3$)alkyl group, the said groups being unsubstituted or substituted with one or more substituents each independently chosen from a ($C_1$-$C_4$)alkoxy group, a hydroxyl group or one or more fluorine atoms;

a trifluoromethyl;

or an $NR_{16}R_{17}$ group;

$R_{12}$ and $R_{13}$ each independently represent a hydrogen atom or a ($C_1$-$C_6$)alkyl group optionally substituted with one or more substituents each independently chosen from a halogen atom, a ($C_3$-$C_7$)cycloalkyl, cyano, —OH or —$OR_{14}$ group;

or $R_{12}$ and $R_{13}$ together with the nitrogen atom to which they are attached constitute a 4- to 7-membered heterocyclic radical which may contain a second heteroatom chosen from a nitrogen, oxygen or sulphur atom;

n represents 0, 1 or 2;

$R_{14}$ represents a ($C_1$-$C_4$)alkyl group which is unsubstituted or substituted with one or more fluorine atoms;

$R_{15}$ represents a hydrogen atom or a ($C_1$-$C_4$)alkyl group;

$R_{16}$ and $R_{17}$ each independently represent:

a hydrogen atom;

or a benzyl group which is unsubstituted or substituted once or several times with a substituent each independently chosen from a halogen atom, a methyl, trifluoromethyl, hydroxyl, ($C_1$-$C_4$)alkoxy or cyano group;

or a ($C_1$-$C_6$)alkyl group which is optionally substituted with one or more halogen atoms, —OH, or —$OR_{14}$ groups;

$R_{18}$ represents a hydrogen atom or a ($C_1$-$C_4$)alkyl group which is unsubstituted or substituted with one or more fluorine atoms;

or its salt.

2. The compound according to claim 1 of formula (I) in which:

$R_1$ and $R_2$ together with the nitrogen atom to which they are attached constitute:

either a piperazin-1-yl or 1,4-diazepan-1-yl radical, the said radicals being substituted with a phenyl, benzodioxolyl, benzodioxolylmethyl, tetrahydrofuranylcarbonyl, —$COR_{11}$, and/or —$CH_2COR_{11}$ group; the phenyl group being itself substituted once or several times with a substituent each independently chosen from a halogen atom, a methyl, trifluoromethyl, hydroxyl, ($C_1$-$C_4$) alkoxy or cyano group;

or a homopiperidin-1-yl, piperidin-1-yl, pyrrolidin-1-yl or azetidin-1-yl radical, the said radicals being substituted once or twice with a substituent each independently chosen from:

a fluorine atom, a cyano, —$COR_{11}$, —$CONR_{12}R_{13}$, —$NR_{12}R_{13}$, $NHCOR_{14}$, —$CH_2COR_{11}$, —$SO_2R_{14}$ group; or —$SO_2 NR_{12}R_{13}$;

or a ($C_1$-$C_4$)alkyl group which is unsubstituted or substituted with one or more substituents each independently chosen from a halogen atom and/or a hydroxyl, or a phenyl or pyridinyl group; the said groups being unsubstituted or substituted once or several times with a substituent each independently chosen from a halogen atom, a methyl, trifluoromethyl, hydroxyl, ($C_1$-$C_4$) alkoxy or cyano group;

or a benzyl group which is substituted once or several times with a substituent each independently chosen from a halogen atom, a methyl, trifluoromethyl, hydroxyl, ($C_1$-$C_4$)alkoxy or cyano group;

or a piperidin-1-yl, pyrrolidin-1-yl or azetidin-1-yl group, the said groups being unsubstituted or substituted once or several times with a substituent each independently chosen from a fluorine atom, a ($C_1$-$C_4$)alkyl, ($C_1$-$C_4$) alkoxy, hydroxyl, trifluoromethyl or —$OCF_3$ group;

or an aminophenyl or aminobenzyl group, the said groups being unsubstituted or substituted once or several times with a substituent each independently chosen from a halogen atom, a methyl, trifluoromethyl, hydroxyl, ($C_1$-$C_4$)alkoxy or cyano group;

or an amino($C_3$-$C_7$)cycloalkyl group which is unsubstituted or substituted once or several times with a substituent each independently chosen from a halogen atom, a hydroxyl, ($C_1$-$C_4$)alkyl, ($C_1$-$C_4$)alkoxy or cyano group, the said $(C_1-C_4)$alkyl group being unsubstituted or substituted once or several times with a fluorine atom;

the other substituents being as defined for the compounds of formula (I);

or its salt.

3. The compound according to claim 1 of formula (I) in which:

$R_1$ and $R_2$ together with the nitrogen atom to which they are attached constitute a homopiperidin-1-yl, piperidin-1-yl, pyrrolidin-1-yl or azetidin-1-yl radical, the said radical being substituted once or twice with a substituent each independently chosen from:

a fluorine atom, a cyano, $-COR_{11}$, $-CONR_{12}R_{13}$, $-NR_{12}R_{13}$, $NHCOR_{14}$, $-CH_2COR_{11}$, $-SO_2R_{14}$ group; or $-SO_2NR_{12}R_{13}$;

or a $(C_1-C_4)$alkyl group which is unsubstituted or substituted with one or more substituents each independently chosen from a halogen atom or a hydroxyl, or a phenyl or pyridinyl group; the said groups being unsubstituted or substituted once or several times with a substituent each independently chosen from a halogen atom, a $(C_1-C_4)$alkyl, trifluoromethyl, hydroxyl, $(C_1-C_4)$alkoxy or cyano group;

or a benzyl group which is substituted once or several times with a substituent each independently chosen from a halogen atom, a $(C_1-C_4)$alkyl, trifluoromethyl, hydroxyl, $(C_1-C_4)$alkoxy and cyano group;

or a piperidin-1-yl, pyrrolidin-1-yl or azetidin-1-yl group, the said groups being unsubstituted or substituted once or several times with a substituent each independently chosen from a fluorine atom, a $(C_1-C_4)$alkyl, $(C_1-C_4)$alkoxy, hydroxyl, trifluoromethyl or $-OCF_3$ group;

or an aminophenyl or aminobenzyl group, the said groups being unsubstituted or substituted once or several times with a substituent each independently chosen from a halogen atom, a $(C_1-C_4)$alkyl, trifluoromethyl, hydroxyl, $(C_1-C_4)$alkoxy or cyano group;

or an amino$(C_3-C_7)$cycloalkyl group which is unsubstituted or substituted once or several times with a substituent each independently chosen from a halogen atom, a hydroxyl, $(C_1-C_4)$alkyl, $(C_1-C_4)$alkoxy or cyano group, the said $(C_1-C_4)$alkyl group being unsubstituted or substituted once or several times with a fluorine atom;

the other substituents being as defined for the compounds of formula (I);

or its salt.

4. The compound according to claim 1 in which A represents an unsubstituted $(C_1-C_5)$alkylene group and $R_9$ represents an $-OR_{12}$, $-NR_{12}R_{13}$, $-CONR_{12}R_{13}$, $-NR_{15}COR_{12}$, $-CONHNH_2$, $-CONHOH$, $-S(O)_nR_{14}$, $-SO_2NR_{12}R_{13}$, $-NR_{18}SO_2R_{14}$, or $-NR_{15}SO_2NR_{12}R_{13}$ group; or its salt.

5. The compound according to claim 1, characterized in that the compound is chosen from the group consisting of:

1-{[1-(4-chlorophenyl)-5-(2,4-dichlorophenyl)-2-(4-hydroxybutyl)-1H-pyrrol-3-yl]carbonyl}-4-phenylpiperidine-4-carboxamide;

1-{[1-(4-chlorophenyl)-5-(2,4-dichlorophenyl)-2-(2-hydroxyethyl)-1H-pyrrol-3-yl]carbonyl}-4-phenylpiperidine-4-carboxamide;

1'-{[1-(4-chlorophenyl)-5-(2,4-dichlorophenyl)-2-(4-hydroxybutyl)-1H-pyrrol-3-yl]carbonyl}-4,4-difluoro-1,4'-bipiperidine-4'-carboxamide;

4-(4-chlorophenyl)-1-{[1-(4-chlorophenyl)-5-(2,4-dichlorophenyl)-2-(3-hydroxy propyl)-1H-pyrrol-3-yl]carbonyl}piperidine-4-carboxamide;

and their salts.

6. A compound of formula (IIter):

(IIter)

in which:

X represents a halogen atom, a hydroxyl, $(C_1-C_4)$alkoxy or benzyloxy group;

and A, $R_3$, $R_4$, $R_5$, $R_6$, $R_7$, $R_8$ and $R_{10}$ are as defined for the compounds of formula (I) according to claim 1.

7. A pharmaceutical composition, characterized in that it comprises a compound of formula (I) according to claim 1 or a pharmaceutically acceptable salt thereof and at least one pharmaceutically acceptable excipient.

* * * * *